(12) United States Patent
Goshayeshgar

(10) Patent No.: US 10,493,247 B2
(45) Date of Patent: Dec. 3, 2019

(54) DEVICES FOR DELIVERING A CHEMICAL DENERVATION AGENT AND METHODS OF USE

(71) Applicant: Medtronic Holding Company Sàrl, Tolochenaz (CH)

(72) Inventor: Mojan Goshayeshgar, Atherton, CA (US)

(73) Assignee: Medtronic Holding Company Sàrl, Tolochenaz (CH)

( * ) Notice: Subject to any disclaimer, the term of this patent is extended or adjusted under 35 U.S.C. 154(b) by 649 days.

(21) Appl. No.: 15/070,195

(22) Filed: Mar. 15, 2016

(65) Prior Publication Data

US 2017/0266419 A1   Sep. 21, 2017

(51) Int. Cl.
| | |
|---|---|
| *A61M 25/10* | (2013.01) |
| *A61B 18/06* | (2006.01) |
| *A61M 25/01* | (2006.01) |
| *A61B 17/00* | (2006.01) |
| *A61B 18/00* | (2006.01) |

(52) U.S. Cl.
CPC .............. *A61M 25/10* (2013.01); *A61B 18/06* (2013.01); *A61M 25/0133* (2013.01); *A61B 17/00234* (2013.01); *A61B 2017/00318* (2013.01); *A61B 2018/0044* (2013.01); *A61B 2018/00577* (2013.01); *A61M 2025/105* (2013.01); *A61M 2210/1003* (2013.01)

(58) Field of Classification Search
CPC .... A61M 2025/105; A61M 2210/1003; A61M 25/0133; A61M 25/10; A61M 25/0138; A61M 25/0147; A61M 39/02; A61B 17/00234; A61B 17/7061; A61B 18/06; A61B 2017/00318; A61B 2018/00154; A61B 2018/00232; A61B 2018/00238; A61B 2018/00339; A61B 2018/00434; A61B 2018/0044; A61B 2018/00577; A61B 2018/00642; A61B 2018/00744
USPC ..................................................... 604/506
See application file for complete search history.

(56) References Cited

U.S. PATENT DOCUMENTS

| | | |
|---|---|---|
| 5,213,576 A | 5/1993 | Abiuso et al. |
| 6,699,242 B2 | 3/2004 | Heggeness |
| 8,361,067 B2 | 1/2013 | Pellegrino |
| 2003/0158517 A1 | 8/2003 | Kokish |
| 2003/0181963 A1 | 9/2003 | Pellegrino et al. |
| 2006/0206178 A1 | 9/2006 | Kim |

(Continued)

FOREIGN PATENT DOCUMENTS

| | | |
|---|---|---|
| AU | 2011218612 A1 | 9/2011 |
| WO | 2013101772 A1 | 7/2013 |
| WO | 2014071161 A1 | 3/2016 |

OTHER PUBLICATIONS

International Search Report and Written Opinion for PCT/2017/022218, the counterpart application dated Jun. 22, 2017, 12 pages.

*Primary Examiner* — Jason E Flick

(57) ABSTRACT

A method for treating back pain in a patient in need of such treatment is provided. The method includes positioning a balloon catheter in or adjacent to a treatment zone containing a basivertebral nerve. A chemical denervation agent is administered with the balloon catheter such that the chemical denervation agent chemically ablates at least a portion of the basivertebral nerve. Kits, systems and methods are disclosed.

20 Claims, 21 Drawing Sheets

(56) References Cited

U.S. PATENT DOCUMENTS

| | | |
|---|---|---|
| 2008/0312637 A1* | 12/2008 | Miller ................ A61B 17/3472 604/512 |
| 2013/0006233 A1 | 1/2013 | Pellegrino et al. |
| 2013/0103022 A1 | 4/2013 | Sutton et al. |
| 2014/0187619 A1 | 7/2014 | Pasricha et al. |
| 2014/0271717 A1* | 9/2014 | Goshayeshgar ..... A61K 9/0085 424/239.1 |

* cited by examiner

DEVICES FOR DELIVERING A CHEMICAL DENERVATION AGENT AND METHODS OF USE

TECHNICAL FIELD

The present disclosure generally relates to medical devices and agents for the treatment of back and/or neck pain, and more particularly to devices for delivering a chemical denervation agent to a target site/treatment zone and methods of use.

BACKGROUND

A vertebra may be damaged due to trauma or disease. Damage of the vertebra may cause end plates of vertebrae to collapse and cause pressure on nerves in the vertebrae resulting in back and/or neck pain. Thus, destroying or interrupting the nerve will result in reduced back pain.

Studies have indicated that the basivertebral nerve conducts pain receptive signals from vertebral endplates adjacent to degenerated disks. This results from the compression or collapse of the vertebral endplates, leading to the compression of basivertebral nerves. Chemical denervation of the lumbar basivertebral nerve may provide relief to patients with chronic lower back pain. However, conventional devices and methods often are unable to effectively navigate close enough to the basivertebral nerve to administer a chemical denervation agent to the basivertebral nerve without causing undue trauma and/or injury to the patient. Thus, there is a need to develop new devices and methods of treating back and/or neck pain caused by the degeneration of vertebral, namely the lumbar region of the spine, that avow accurate and precise delivery of chemical denervation agents at, near, or in the damaged area of the vertebra in order to minimize physical and psychological trauma to the patient while effectively reducing or eliminating back and/or neck pain.

SUMMARY

New devices and methods are provided for the treatment of back and/or neck pain that allow accurate and precise delivery of chemical denervation agents at, near, or in a damaged area of a vertebra, which results in minimal physical and psychological trauma to the patient and reductions in back and/or neck pain.

In some embodiments, the methods include utilizing devices to deliver a chemical denervation agent to treat back and/or neck pan in a patient in need of such treatment is provided. The devices are configured to deliver a chemical denervation agent to an effective treatment zone comprising a nerve at a target region of the spine so as to chemically ablate and/or denervate a nerve, such as, for example, a basivertebral nerve.

In some embodiments, the methods include positioning a balloon catheter in or adjacent to a treatment zone containing a basivertebral nerve and administering a chemical denervation agent with the balloon catheter such that the chemical denervation agent chemically ablates at least a portion of the basivertebral nerve. In some embodiments, the chemical denervation agent is delivered within 1 mm of the basivertebral nerve. In some embodiments, the chemical denervation agent is or is part of a flowable composition. In some embodiments, the chemical denervation agent is or is part of a drug depot.

In some embodiments, a balloon of the balloon catheter is positioned within the treatment zone, such as, for example a vertebra. In some embodiments, the balloon moves from an unexpanded or uninflated configuration to an expanded or inflated configuration within the vertebra. In some embodiments, the balloon increases the exposed surface when the balloon is in the expanded configuration. In some embodiments, the balloon moves from the unexpanded configuration to the expanded configuration by injecting a chemical denervation agent inside the balloon. In some embodiments, the chemical denervation agent diffuses through the balloon to deliver the chemical denervation agent at, near, or in the damaged area of the vertebra, such as, for example, a basivertebral nerve. In some embodiments, the chemical denervation agent moves through pores the balloon to deliver the chemical denervation agent at, near, or in the damaged area of the vertebra. In some embodiments, the pores in the balloon form as a material that the balloon is made from degrades to prolong the release of the chemical denervation agent. In some embodiments, the chemical denervation agent is released over a few days. In some embodiments, the chemical denervation agent is released over one or more weeks.

In some embodiments, the balloon is at least partially coated with the chemical denervation agent. In some embodiments, the balloon is configured to remain within the patient after an incision in the patient through which the balloon catheter is inserted is closed. In some embodiments, the balloon catheter includes a one-way valve to avow the balloon to remain inflated within the patient after other components of the balloon catheter are detached from the balloon and removed from the patient through the incision.

In some embodiments, the chemical denervation agent moves through a lumen of the balloon catheter and exits a port of the balloon catheter so as to deliver the chemical denervation agent at, near, or in the damaged area of the vertebra, such as, for example, a basivertebral nerve.

In some embodiments, the balloon is coupled to a shaft that is flexible to allow the balloon catheter to be moved along a curved path. In some embodiments, the balloon catheter is steerable to allow the shaft to be selectively bent at portions of the shaft to assist the balloon catheter in moving along the curved path. In some embodiments, the curved path is created by a medical practitioner.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

The present disclosure will become more readily apparent from the specific description accompanied by the following drawings, in which.

DETAILED DESCRIPTION

Figure 1:
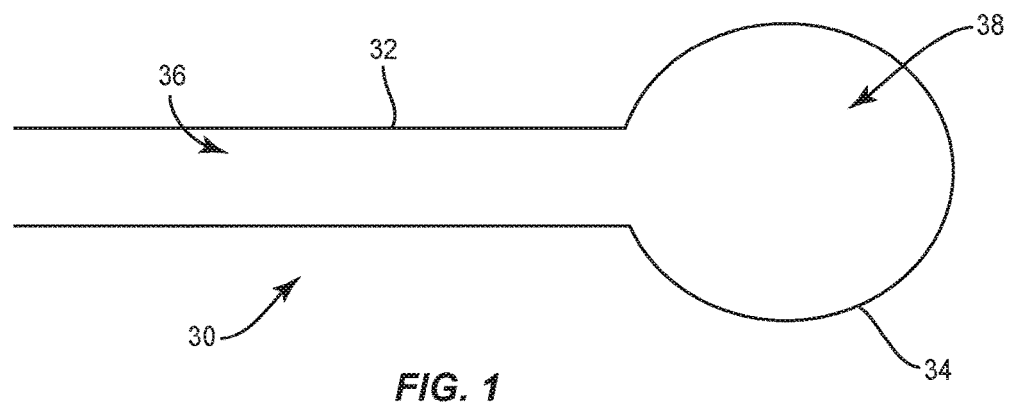
FIG. 1 is a side, cross sectional view of components of one embodiment of a balloon catheter in accordance with the principles of the present disclosure.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claim are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

Definitions

It is noted that, as used in this specification and the appended claims, the singular forms "a," "an," and "the,"

include plural referents unless expressly and unequivocally limited to one referent. Thus, for example, reference to "a chemical denervation agent" or a "device" includes one, two, three or more chemical denervation agents or one, two, three or more devices.

A "chemical denervation agent", includes, but is not limited to an agent that temporarily or permanently blocks neural transmission to reduce chronic pain in the patient, such as for example, the ablation of the basivertebral nerve in the treatment zone of a vertebral body to reduce back and/or neck pain, such as, for example, chronic back and/or neck pain. For example, in some embodiments the chemical denervation agent can be a neurolytic agent such as Ethanol or a neurotoxin agent such as Botulinum Toxin, Localized drug delivery may also include products including magnetic nano particles that contain neurotoxins like for example Botox B.

The chemical denervation agent can include one or more analgesic. "Analgesic" refers to an agent or compound that can reduce, relieve or eliminate, pain. Examples of analgesic agents include but are not limited to acetaminophen, a local anesthetic, such as for example, lidocaine, bupivacaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, mepiridine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof. Analgesic agents also include those with analgesic', and anti-inflammatory properties, such as, for example, amitriptyline, carbamazepine, gabapentin, pregabalin, clonidine, or a combination thereof. The device can include one or more analgesics.

The chemical denervation agent can include one or more anti-inflammatory agent. The phrase "anti-inflammatory agent" refers to an agent or compound that has anti-inflammatory effects. These agents may remedy pain by reducing inflammation. Examples of anti-inflammatory agents include, but are not limited to, a statin, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic add, naproxen, phenylbutazone, piroxicam, meloxicam, salicylamide, salicylic acid, desoxysulindac, tenoxicam, ketorolac, clonidine, flufenisal, salsalate, triethanolamine salicylate, aminopyrine, antipyrine, oxyphenbutazone, apazone, cintazone, flufenamic add, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbarnate, or a combination thereof. Anti inflammatory agents also include other compounds such as steroids, such as for example, fluocinolone, cortisol, cortisone, hydrocortisone, fludrocortisone, prednisone, prednisolone, methylprednisolone, triamcinolone, betamethasone, dexamethasone, beclomethasone, fluticasone interleukin-1 receptor antagonists, thalidomide (a TNF-α release inhibitor), thalidomide analogues (which reduce TNF-α production by macrophages), bone morphogenetic protein (BMP) type 2 or BMP-4 (inhibitors of caspase 8, a TNF-α activator), quinapril (an inhibitor of angiotensin II, which upregulates INF-α), interferons such as IL-11 (which modulate TNF-α receptor expression), and aurin-tricarboxylic acid (which inhibits TNF-α), guanidinoethyldisulfide, or a combination thereof.

Exemplary anti-inflammatory agents include, for example, naproxen; diclofenac; celecoxib; sulindac; diflunisal; piroxicam; indomethacin; etodolac; meloxicam; ibuprofen; ketoprofen; r-flurbiprofen; mefenamic; nabumetone; tolmetin, and sodium salts of each of the foregoing; ketorolac bromethamine; ketorolac tromethamine; ketorolac acid; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isomers); methyl, ethyl, propyl, isopropyl, n-butyl, sec-butyl, t-butyl, esters of acetylsalicylic acid; tenoxicam; aceclofenac; nimesulide; nepafenac; amfenac; bromfenac; flufenamate; phenylbutazone, or a combination thereof.

The chemical denervation agent can include one or more steroids, including, for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

The chemical denervation agent can include one or more statins. Examples of useful statins for treatment of pain and/or inflammation include, but are not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin. Anti-inflammatory agents also include those with anti-inflammatory properties, such as, for example, amitriptyline, carbamazepine, gabapentin, pregabalin, clonidine, or a combination thereof.

In some embodiments, the anti-inflammatory agent can include an "anti-cytokine agent." An anti-cytokine agent includes any molecule, cell, or physical stimulus which decreases, blocks, inhibits, abrogates or interferes with the pro-inflammatory cascade of cytokine proteins leading to an inflammatory response. For example, a suitable "tumor necrosis factor alpha antagonist" or "TNF-alpha" antagonist can bind TNF, and includes anti-TNF antibodies and/or receptor molecules which bind specifically to TNF. A suitable TNF antagonist can also prevent or inhibit TNF synthesis and/or TNF release and includes compounds such as thalidomide, tenidap, or phosphodiesterase inhibitors, such as, but not limited to, pentoxifylline or rolipram.

Anti-cytokine agents include substances that are direct and local-acting modulators of the pro-inflammatory effect of TNF-alpha, such as but not limited to, soluble tumor necrosis factor alpha receptors, any pegylated soluble tumor necrosis factor alpha receptor, monoclonal or polyclonal antibodies or antibody fragments or combinations thereof. Suitable examples include but are not limited to Adalimumab, Infliximab, Etanercept, Pegsunercept (PEG sTINF-R1), sTNF-R1, CDP-870, CDP-571, CNI-1493, RDP58, ISIS 104838, 1, 3-beta-D-glucans, Lenercept, PEG-sTNFRII Fc Mutein, D2E7, Afelimomab, or combinations thereof. They can decrease pain through their actions as inhibitors or agonists of the release of pro-inflammatory molecules. For example, these substances can act by inhibiting or antagonizing expression or binding of cytokines or other molecules that act in the early inflammatory cascade, often resulting in the downstream release of prostaglandins and leukotrienes. These substances can also act, for example, by blocking or antagonizing the binding of excitatory molecules to nociceptive receptors in the nervous system or neuromuscular system, as these receptors often trigger an inflammatory response to inflammation or injury of the nerve or surrounding tissue through a nitric oxide-mediated mechanism. These biological response modifiers include, for example, inhibitors of the action of tumor necrosis factor alpha (TNF-alpha).

In some embodiments, the anti-cytokine agent is a TNF binding protein. One suitable such anti cytokine agent is currently referred to as Onercept, Onercept-like agents, and derivatives are all considered acceptable. Still other suitable anti-cytokine agents include dominant-negative TNF variants. A suitable dominant-negative TNF variant includes but is not limited to DN-TNF and including those described by Steed et al. (2003), "Inactivation of TNF signaling by rationally designed dominant-negative TNF variants," Science, 301(5641):1895-1898. Still more embodiments include the use of a recombinant adeno-associated viral (rAAV) vector technology platform to deliver the oligonucleotides encoding inhibitors, enhancers, potentiators, neutralizers, or other modifiers. For example, in one embodiment a rAAV vector technology platform delivers the DNA sequence of a potent inhibitor of tumor necrosis factor (TNF-alpha). One suitable inhibitor is TNFR:Fc, Other anti-cytokine agents interfere with one of the steps in the gene expression and secretion of cytokines, such as transcription, translation, folding, post-translational modification, and intracellular transport. For example, small antisense RNA or short interfering RNA (siRNA) can block post-transcriptional processing of cytokine genes. Other anti-cytokine agents include antibodies, including but not limited to naturally occurring or synthetic, double chain, single chained, or fragments thereof. For example, suitable anti-cytokine agents include molecules are based on single chain antibodies called Nanobodies® (Ablynx, Ghent Belgium) which are defined as the smallest functional fragment of a naturally-occurring single domain antibody.

It is understood that TNF is both affected by upstream events which modulate its production and, in turn, affects downstream events. Alternative approaches to treating chronic back pain include using antagonists designed to specifically target TNF as well as molecules upstream, downstream and/or a combination thereof. Such approaches include, but are not limited to modulating TNF directly, modulating kinases, inhibiting cell-signaling, manipulating second messenger systems, modulating kinase activation signals, modulating a duster designator on an inflammatory cell, modulating other receptors on inflammatory cells, blocking transcription or translation of TNF or other targets in pathway, modulating TNF-alpha post-translational effects, employing gene silencing, or modulating interleukins, for example IL-1, IL-6 and IL-8.

Interleukin-1 is a pro-inflammatory cytokine similar in action to TNF-alpha. For example, certain inhibitors of this protein are similar to those developed to inhibit TNF-alpha. One such example is Kineret® (anakinra) which is a recombinant, non-glycosylated form of the human interleukin-1 receptor antagonist (IL-1 Ra). Another suitable anti-cytokine agent is AMG 108, which is a monoclonal antibody that blocks the action of IL-1.

Other suitable anti-cytokine agents include: integrin antagonists, alpha-4 beta-7 integrin antagonists, cell adhesion inhibitors, interferon gamma antagonists, CTLA4-lg agonists/antagonists (BMS-188667), CD40 ligand antagonists, Humanized anti-IL-6 mAb (MRA, Tocilizurnab, Chugai), HMGB-1 mAb (Critical Therapeutics Inc.), anti-IL2R antibody (daclizumab, basilicimab), ABX (anti IL-8 antibody), recombinant human IL-10, and HuMax IL-15 (anti-IL 15 antibody).

Unless otherwise specified or apparent from context, where this specification and the set of claims that follows refer to a drug (e.g., a chemical denervation agent) the inventor(s) are also referring to a pharmaceutically acceptable salt of the drug including stereoisomers. Pharmaceutically acceptable salts include those salt-forming acids and bases that do not substantially increase the toxicity of the compound. Some examples of potentially suitable salts include salts of alkali metals such as magnesium, calcium, sodium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, p-toluenesulfonic acids, or the like.

"Treating" or treatment of a disease or condition refers to executing a protocol, which may include administering one or more drugs, such as a chemical denervation agent, to a patient (human, normal or otherwise, or other mammal), in an effort to alleviate signs or symptoms of the disease. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms, does not require a cure, and specifically includes protocols that have only a marginal effect on the patient. "Reducing pain" includes a decrease in pain and does not require complete alleviation of pain signs or symptoms, and does not require a cure. In various embodiments, reducing pain includes even a marginal decrease in pain. By way of example, the administration of a medical device (e.g., drug depot) containing a chemical denervation agent degrades the basivertebral nerve in the lumber vertebrae of a patient, which reduces or alleviates chronic back pain, in some embodiments, additional agents administered with the chemical denervation agent, reduces pain and/or inflammation.

"Localized" delivery includes delivery where one or more chemical denervation agents are deposited within a tissue, for example, a lumbar vertebrae, in close proximity (within about 5 cm, or preferably within about 2 cm, for example, to a nerve such as the basivertebral nerve. In some embodiments, a device, such as, for example, an inflatable balloon and/or balloon catheter can be used to deliver a chemical denervation agent to an area containing a nerve to be ablated. A "targeted delivery system" provides delivery of one or more chemical denmation agents at or near the target site as needed for nerve ablation and/or treatment of pain, inflammation or other disease or condition.

The term "mammal" refers to organisms from the taxonomy class "mammalian," including but not limited to humans, other primates such as chimpanzees, apes, orangutans and monkeys, rats, mice, cats, dogs, cows, horses, etc. In various embodiments, the mammal is a human patient.

Chemical Denervation Agent

New compositions and methods of treating back and/or pain are provided that avow accurate and precise delivery of a chemical denervation agent at, near, or in the nerve to be ablated and/or denervated to minimize physical and psychological trauma to the patient.

By the administration of a chemical denervation agent via a delivery device, such as, for example, an inflatable balloon or balloon catheter, precise delivery of the chemical denervation agent at, near, or in the nerve to be ablated and/or denervated can be accomplished. The chemical denervation agent ablates and/or denervates the nerve, for example, the basivertebral nerve, to temporarily or permanently block neural transmission of the treatment zone to reduce back and/or pain in the patient.

In some embodiments, the chemical denervation agent includes one or more neurolytic agents such as Ethanol or a neurotoxin agent such as Botulinum Toxin. In some embodiments, the chemical denervation agent includes products, such as, for example, magnetic nano particles that contain neurotoxins like for example Botox B.

In some embodiments, the chemical denervation agent is administered in an amount sufficient to maintain a pharmacologically active level of the chemical denervation agent locally at the site of implantation in an amount to degrade at least a portion of the basivertebral nerve of the lumbar vertebrae which reduces or blocks neural transmission of the nerve. This will reduce pain and/or inflammation at the site. For example, one or more chemical neurological agent is used to ablate and/or denervate the nerve at each level. In some embodiments, the amount of chemical denervation agent released from the balloon catheter is released as an initial burst and then over time.

In some embodiments, the chemical denervation agent is hyaluronidase. Hyaluronidase is available from various manufactures and is described in U.S. Pat. Nos. 7,767,429; 7,169,405; 7,132,098; 7,572,440; 6,958,149; and U.S. Publication Nos. US20040268425; 0320100003238; US20090214505; US20100003237; and WO/2009/111066. The entire disclosures of these patents and publications are herein incorporated by reference in their entireties into the present disclosure. One suitable form of hyaluronidase is available from Halozyme Therapeutics, Inc. (IL USA), which is a recombinant human hyaluronidase glycoprotein enzyme platform (rHuPH20). The hyaluronidase can be pegylated or a pegylated variant.

In some embodiments, a drug, such as, for example, the chemical denervation agent is administered with one or more additional therapeutic agents (e.g., growth factor, analgesic, anti-inflammatory agent, etc.). The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of a chemical denervation agent as well as an anti-inflammatory agent for delivery to the site. In some embodiments, the drug provides an optimal drug concentration gradient at a distance of up to about 0.1 cm to about 5 cm from the implant site, and comprises at least one therapeutic agent or its pharmaceutically acceptable salt.

The term "therapeutic agent" includes any molecule, protein, growth factor, etc. which would be contemplated for administration in, at or near the basivertebral nerve in at least one vertebra. This would be delivered in addition to the chemical denervation agent. Such examples would include, but are not limited to one or more growth factors, anti-inflammatory agents (e.g., NSAIDS), antibiotics, analgesics, muscle relaxants, or the like, as well as any molecule or cell, which decreases, blocks, inhibits, abrogates or interferes with the pro-inflammatory cascade of proteins leading to an inflammatory response. For example, a suitable TNF-α antagonist can bind TNF-α, and includes anti TNF-α antibodies and/or receptor molecules which bind specifically to TNF-α, as well as small molecules which antagonize TNF-α activity. A suitable TNF-α antagonist can also prevent or inhibit TNF-α synthesis and/or TNF-α release. Another example may also provide for any cytokine or biologically active fragment thereof which possesses the ability to decrease, block, inhibit, abrogate or interfere with the pro-inflammatory response promoted by other cytokine proteins (e.g., IL-10, IL-4, IL-13 and TGF-β) as well as any molecule, cell, which positively modulates the anti-inflammatory effect of such an anti-inflammatory cytokine so as to impart an increase in the ability to reduce patient inflammation and/or pain.

The therapeutic agent may comprise growth factors that modulate the growth or differentiation of other cells, particularly connective tissue progenitor cells. The therapeutic agent may include, but is not limited to, members of the fibroblast growth factor family, including acidic and basic fibroblast growth factor (FGF-1 and FGF-2) and FGF-4, members of the platelet-derived growth factor (PDGF) family, including PDGF-AB, PDGF-BB and PDGF-AA; EGFs; the TGF-3 superfamily, including TGF-β1, 2 or 3; osteoid-inducing factor (OIF); angiogenin(s); endothelins; hepatocyte growth factor or keratinocyte growth factor; members of the bone morphogenetic proteins (BMP's) BMP-1, BMP-3, BMP-2; OP-1, BMP-2A, BMP-2B, or BMP-7; HBGF-1 or HBGF-2; growth differentiation factors (GDF's); members of the hedgehog family of proteins, including Indian, sonic and desert hedgehog; ADMP-1; other members of the interleukin (IL) family; or members of the colony-stimulating factor (CSF) family, including CSF-1, G-CSF, and GM-CSF, or isoforms thereof; or VEGF, NELL-1 (neural epidermal growth factor-like 1), CD-RAP (cartilage-derived retinoic acid-sensitive protein) or combinations thereof.

In some embodiments, growth factors (e.g., osteogenic protein) may be administered with the chemical denervation agent and/or the chemical denervation agent may include one or more growth factors. Exemplary osteogenic proteins include, but are not limited to, OP-1, OP-2, OP-3, BMP-2, BMP-3, BMP-3b, BMP-4, BMP-5, BMP-6, BMP-9, BMP-10, BMP-11, BMP-12, BMP-13, BMP-14, BMP-15, GDF-1, GDF-2, GDF-3, GDF-5, GDF-6, GDF-7, GDF-8, GDF-9, GDF-10, GDF-11, GDF-12, CDMP-1, CDMP-2, CDMP-3, DPP, Vg-1, Vgr-1, 60A protein, NODAL, UNIVIN, SCREW, ADMP, NEURAL, and TGF-beta. As used herein, the terms "morphogen," "bone morphogen," "BMP," "osteogenic protein" and "osteogenic factor" embrace the class of proteins typified by human osteogenic protein 1 (hOP-1) and are described in U.S. Pat. No. 7,572,440. The entire disclosure is hereby incorporated by reference in the present disclosure.

Exemplary growth factors include, but are not limited to, members of the transforming growth factor beta family, including bone rnorphogenetic protein 2 (BMP-2); bone morphogenetic protein 4 (BMP-4); and transforming growth factors beta-1, beta-2, and beta-3 (potent keratinocyte growth factors). Other useful members of the transforming growth factor beta family include BMP-3, BMP-5, BMP-6, BMP-9, DPP, Vg1, Vgr, 60A protein, GDF-1, GDF-3, GDF-5, GDF-6, GDF-7, CDMP-1, CDMF-2, CDMP-3, BMP-10, BMP-11, BMP-13, BMP-15, Univin, Nodal, Screw, ADMP, Neural, and amino acid sequence variants thereof. Other growth factors include epidermal growth factor (EGF), which induces proliferation of both mesodermal and ectodermal cells, particularly keratinocytes and fibroblasts; platelet-derived growth factor (PDGF), which exerts proliferative effects on mesenchymal cells; fibroblast growth factor (FGF), both acidic and basic; and insulin-like growth factor 1 (IGF-1) or 2 (IGF-2), which mediate the response to growth hormone, particularly in bone growth. Further growth factors include osteogenic proteins. A particularly preferred osteogenic protein is OP-1, also known as bone morphogenetic protein 7 (BMP-7). OP-1 is a member of the transforming growth factor beta gene superfamily. It is a 139 amino acid residue long homodimer of MW 36,000. OP-1 induces new bone formation in vivo and promotes the repair of diaphyseal segmental bone defects and is described in U.S. Pat. No. 7,132,098. The entire disclosure is hereby incorporated by reference in the present disclosure.

In some embodiments, the chemical denervation agent may be administered or delivered with cells. In some embodiments, the chemical denervation agent includes cells. Suitable cells include, without limitation, mesenchymal stem cells, periosteal cells, pluripotent stem cells, embryonic stem cells, osteoprogentior cells, osteoblasts, osteoclasts, bone marrow-derived cell lines, or any combination thereof. Other therapeutic agents include, for example, DNA, RNA, and their derivatives, vehicles for gene therapy, agents for inducing cell differentiation or de-differentiation or the like.

In some embodiments, the chemical denervation agent may be administered or delivered with nutrients such as chondroitin sulfate and/or glucosamine. In some embodiments, the chemical denervation agent includes nutrients such as chondroitin sulfate and/or glucosamine. In some embodiments, the chemical denervation agent may be administered or delivered with a lubricant including, but not limited to, lubricin, polyethylene glycol, or any combinations thereof. In some embodiments, the chemical denervation agent includes a lubricant including, but not limited to, lubricin, polyethylene glycol, or any combinations thereof.

In some embodiments, the chemical denervation agent may be administered or delivered with at least one analgesic agent or its pharmaceutically acceptable salt. In some embodiments, the chemical denervation agent includes at least one analgesic agent or its pharmaceutically acceptable salt. Examples of analgesic agents include but are not limited to acetaminophen, a local anesthetic, such as for example, lidocaine, bupivacaine, ropivacaine, opioid analgesics such as amitriptyline, carbamazepine, gabapentin, pregabalin, clonidine, opioid analgesics or a combination thereof. Opioid analgesics include, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol or a combination thereof. Analgesic-agents also include those with analgesic and anti-inflammatory properties, such as, for example, amitriptyline, carbamazepine, gabapentin, pregabalin, clonidine, or a combination thereof.

In some embodiments, the chemical denervation agent may be administered or delivered with anti-inflammatory agents and/or an analgesic, comprising flurbiprofen, indoprofen, naproxol, pentazocine, proxazole, tramadol, verilopam, volazocine, xylazine, zucapsaicin, phenyhydantoin, phenobarbital, primidone, ethosuximide, methsuximide, phensuximide, trimethadione, diazepam, benzodiazepines, phenacemide, pheneturide, acetazolamide, sulthiame, bromide, nalorphine, naloxone, naltrexone, salycilates, phenylbutazone, indomethacin, phenacetin, dextropropoxyphene, levomethadyl, pethidine, remifentanil, flupirtine or a combination thereof. In some embodiments, the chemical denervation agent includes one or more of the anti-inflammatory agents and/or analgesics discussed herein.

In some embodiments, the anti-inflammatory and/or analgesic agents include, but are not limited to, salicylates, diflunisal, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone, protein inhibitors of TNF, such as etanercept, Remicade, IL-1, such as Kineret®, p38, RANK, RANKL or a combination thereof.

In some embodiments, the chemical denervation agent may be administered or delivered with at least one analgesic agent or its pharmaceutically acceptable salt and/or at least one anti-inflammatory agent or its pharmaceutically acceptable salt and may be co-administered with a muscle relaxant. Co-administration may involve administering at the same or separately (e.g., in sequence). In some embodiments, the chemical denervation agent includes at least one analgesic agent or its pharmaceutically acceptable salt and/or at least one anti-inflammatory agent or its pharmaceutically acceptable salt.

Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

In some embodiments, the chemical denervation agent may be administered or delivered with other therapeutic agents or active ingredients. In some embodiments, the chemical denervation agent includes therapeutic agents or active ingredients. Suitable additional therapeutic agents include, but are not limited to, integrin antagonists, alpha-4 beta-7 integrin antagonists, cell adhesion inhibitors, interferon gamma antagonists, CTLA4-lg agonists/antagonists (BMS-188667), CD40 ligand antagonists, Humanized anti-IL-6 mAb (MRA, Tocilizurnab, Chugai), HMGB-1 mAb (Critical Therapeutics Inc.), anti-IL2R antibodies (daclizurnab, basilicimab), ABX (anti IL-8 antibodies), recombinant human IL-10, or HuMax IL-15 (anti-IL 15 antibodies).

Other suitable therapeutic agents include at least one anti-inflammatory agent or analgesic agent include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. It is contemplated that where desirable a pegylated form of the above may be used. Examples of other therapeutic agents include NF kappa B inhibitors such as glucocorticoids, antioxidants, such as dilhiocarbamate.

In some embodiments, the methods provided can be used to treat patients with mild to moderate degeneration of vertebrae so that two end plates of the vertebrae collapse towards each other putting pressure on the basivertebral nerve. As explained herein, delivery of the chemical denervation agent may be accomplished with little or no additional injury to the patient. In some embodiments, the methods provided herein may be especially useful for patients that are not good candidates for other treatments, such as, surgery, spinal fixation, vertebrae replacement, spinal fusion, and other surgical regimens for the treatment of degenerated vertebral disease.

Accordingly, in some embodiments, there is a method for treating a back and/or neck pain by chemical denervation of the basiverebral nerve, the method comprising administering a chemical denervation agent to the effective area comprising the basivertebral nerve to proteolytically degrade at least a portion of the basivertebral nerve.

A skilled artisan will be capable of determining the desired amount of chemical denervation agent based on a number of factors, including, for example, the degree of vertebrae/disc degeneration, the age, weight, and health of the patient, and the degree of restoration required. Additionally, the methods provided herein may be used to slow the rate of progressive collapse of vertebrae and/or maintain the height of a vertebrae experiencing progressive collapse.

Delivery Devices

A chemical denervation agent, such as, for example, one of the chemical denervation agents discussed herein may be delivered to a target site or area, such as, for example a basivertebral nerve, using a delivery device, such as, for example, a balloon catheter 30. The chemical denervation agent may be delivered to the basivertebral nerve by itself or with other therapeutic agents, such as, for example, one or more of the therapeutic agents discussed herein.

In some embodiments, the components of balloon catheter 30 can be fabricated from biologically acceptable materials suitable for medical applications, including metals, synthetic polymers, ceramics and bone material and/or theft composites, depending on the particular application and/or preference of a medical practitioner. For example, the components of balloon catheter 30, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastio metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaelohe and their combinations.

Various components of balloon catheter 30 may have material composites, including the above materials, to achieve various desired characteristics such as strength, rigidity, elasticity, compliance, biomechanical performance, durability and radiolucency or imaging preference. The components of balloon catheter 30, individually or collectively, may also be fabricated from a heterogeneous material such as a combination of two or more of the above-described materials. The components of balloon catheter 30 may be monolithically formed, integrally connected or include fastening elements and/or instruments, as described herein.

In one embodiment, shown in FIG. 1, balloon catheter 30 includes a cylindrical portion 32 and a balloon 34 coupled to cylindrical portion 32. Cylindrical portion 32 is hollow and defines a passageway 36 that is in communication with an internal chamber 38 of balloon 34 to move balloon 34 from an unexpanded configuration, such as, for example, an uninflated configuration (FIGS. 1, 1A and 3) to an expanded configuration, such as, for example, an inflated configuration (FIG. 4). That is, a material may be moved through passageway 36 and into chamber 38 to move balloon 34 from the uninflated configuration to the inflated configuration. When balloon 34 is in the inflated configuration, balloon 34 has a maximum diameter that is greater than the maximum diameter of balloon 34 when balloon 34 is in the uninflated configuration. In some embodiments, the material that is used to inflate balloon 34 is a chemical denervation agent, such as, for example, one or more of the chemical denervation agents discussed herein. In some embodiments, the material that is used to inflate balloon 34 is a gas, such as, for example, air. In some embodiments, the material is a liquid, such as, for example, saline or water.

In some embodiments, cylindrical portion 32 is a hollow shaft or tube. In some embodiments, cylindrical portion 32 is flexible to allow cylindrical portion 32 to bend as cylindrical portion 32 is navigated through a patient's anatomy. For example, cylindrical portion 32 may be flexible to allow cylindrical portion 32 to be navigated along a curved path created by a medical practitioner in order to position balloon 34 at, in or near a target location or treatment zone, such as, for example, a basivertebral nerve. In embodiments wherein cylindrical portion 32 is flexible, cylindrical portion 32 can be bent without breaking cylindrical portion 32. In some embodiments, cylindrical portion 32 is rigid such that cylindrical portion 32 cannot be bent without cylindrical portion 32 breaking. For example, cylindrical portion 32 may be rigid to provide strength to cylindrical portion 32 in applications wherein balloon catheter 30 is navigated along a straight path created by a medical practitioner in order to position balloon 34 at, in or near a target location or treatment zone, such as, for example, a basivertebral nerve.

In some embodiments, balloon 34 is made from a resilient biocompatible material. In one embodiment, balloon 34 is a compliant balloon that resists stretching. In one embodiment, balloon 34 comprises polyolefin copolymer (POC). In one embodiment, balloon 34 is a non-compliant balloon that stretches, at least to some degree. In one embodiment, balloon 34 comprises polyethylene terapthelate (PET). In some embodiments, balloon 34 can have various cross section configurations when balloon 34 is hi the inflated configuration, such as, for example, oval, oblong, triangular, rectangular, square, polygonal, irregular, uniform, non-uniform, variable, tubular and/or tapered. In some embodiments, an outer surface of balloon 34 may have various surface configurations, such as, for example, smooth and/or surface configurations to enhance fixation with tissue, such as, for example, rough, arcuate, undulating, porous, semi-porous, dimpled, polished and/or textured.

Balloon 34 can be a single or a multi-layered balloon, where each balloon layer has the same diameter and/or wall thickness, is comprised of the same material or materials having substantially identical mechanical properties, and has the same degree of molecular orientation in the body portion of the balloon. It will be apparent that in some situations it will be desirable to have some balloon layers having different thicknesses, materials, and/or degree of molecular orientations upon deflation, while at the same time having equivalent size, mechanical properties, and/or orientation upon inflation.

Figure 1A:
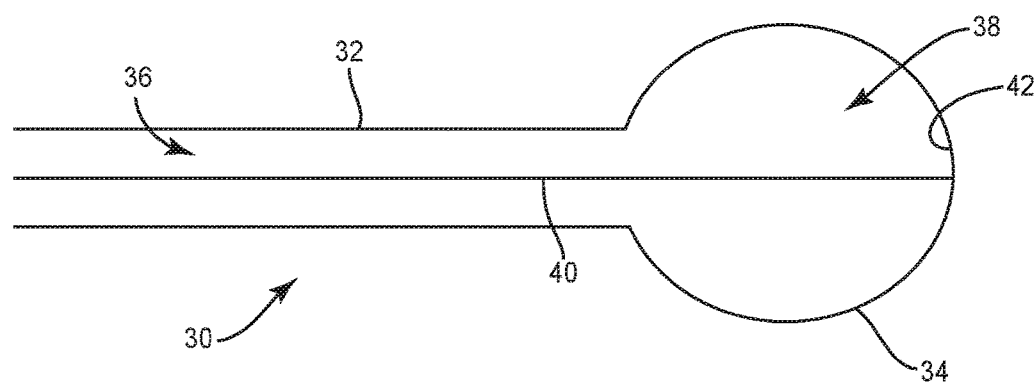
FIG. 1A is a side, cross sectional view of components of one embodiment of a balloon catheter in accordance with the principles of the present disclosure.
Figure 1B:
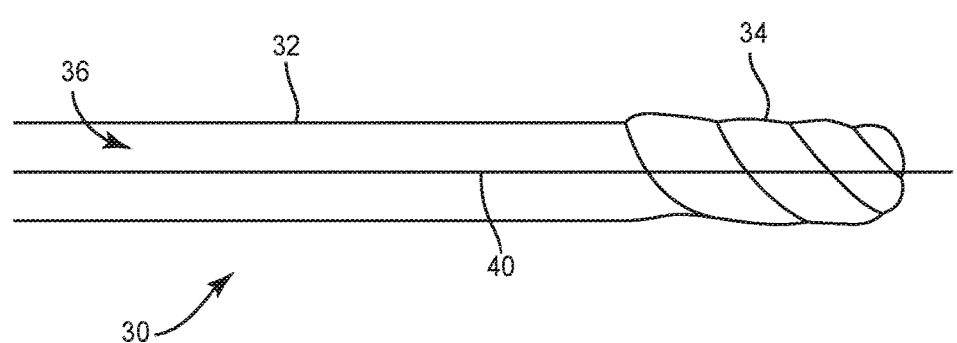
FIG. 1B is a side, cross sectional view of the balloon catheter shown in FIG. 1A.

In some embodiments, as shown in FIGS. 1A and 1B, balloon catheter 30 includes a cord or wire, such as, for example, a stylet 40 that extends through passageway 36 and into chamber 38, as shown in FIG. 1A. A distal end of stylet 40 is fixed to an inner surface 42 of balloon 34 that defines chamber 38. This configuration allows the maximum diameter of balloon 34 to be reduced. For example, balloon 34 may move from a first maximum diameter when balloon 34 is in the uninflated configuration (FIG. 1A) to a second maximum diameter when balloon 34 is in the uninflated configuration (FIG. 1B). In some embodiments, balloon 34 is fixed to cylindrical portion 32 such that rotating stylet 40 about an axis defined by stylet 40 in a clockwise or counterclockwise direction causes balloon 34 to twist to reduce the diameter of balloon 34 from the first maximum diameter (FIG. 1A) to the second maximum diameter (FIG. 1B).

Figure 2:
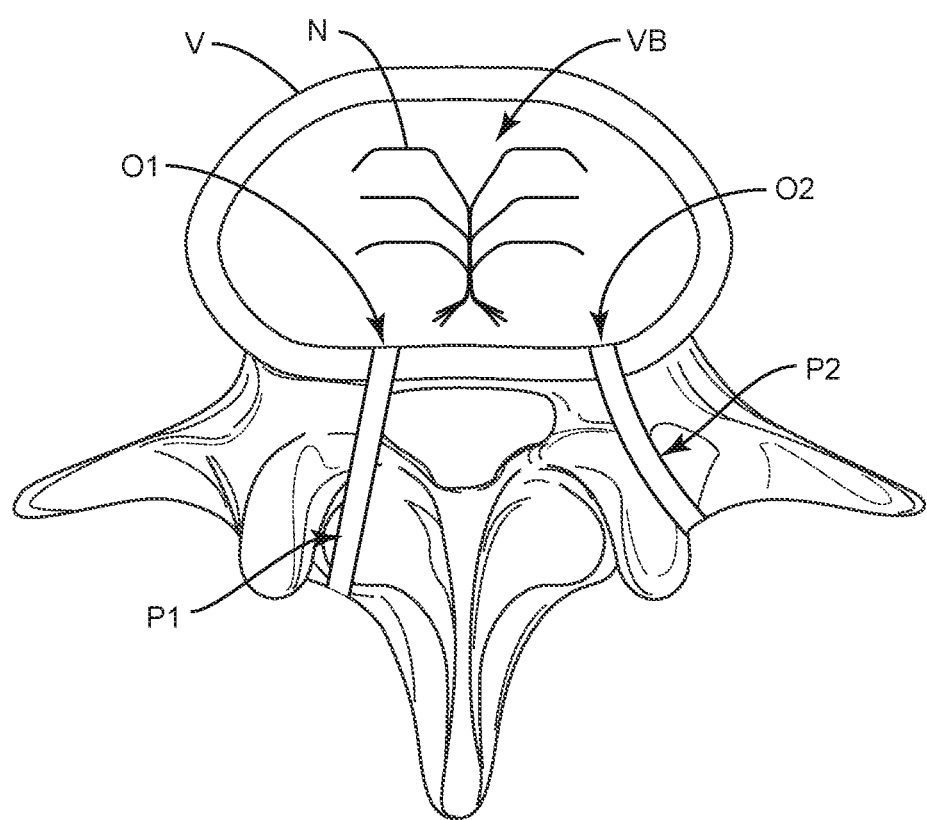
FIG. 2 is a top, cross sectional view of a vertebra.
Figure 3:
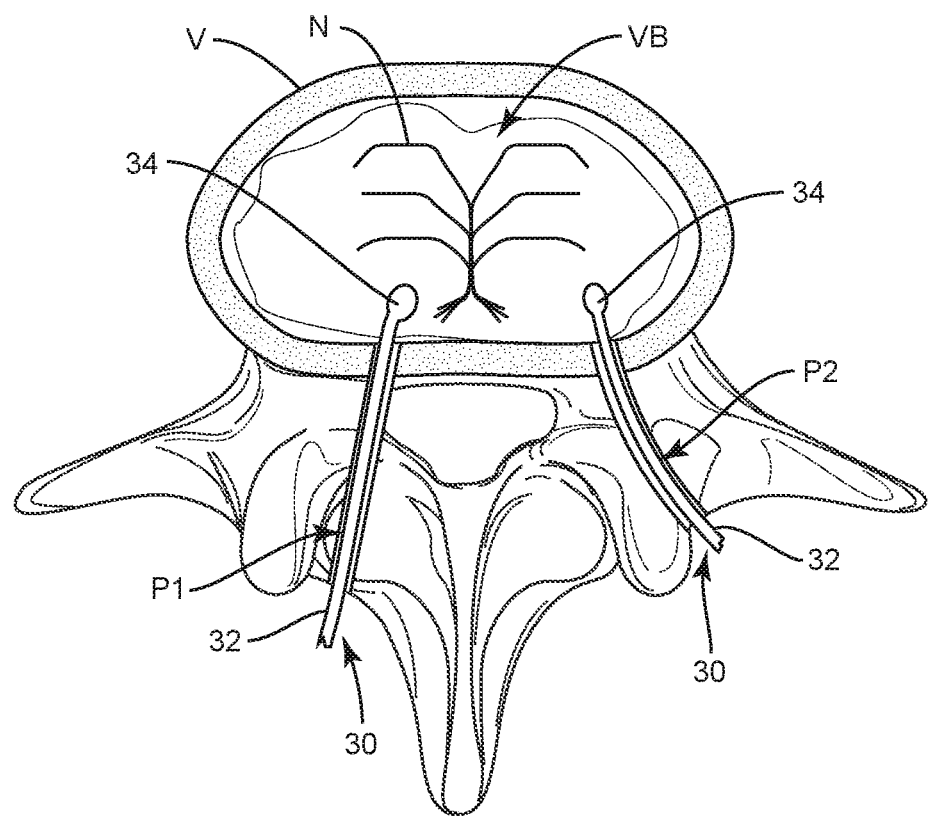
FIG. 3 is a top, cross sectional view of the vertebra shown in FIG. 3 with components of one of the balloon catheters discussed herein inserted into the vertebra.
Figure 4:
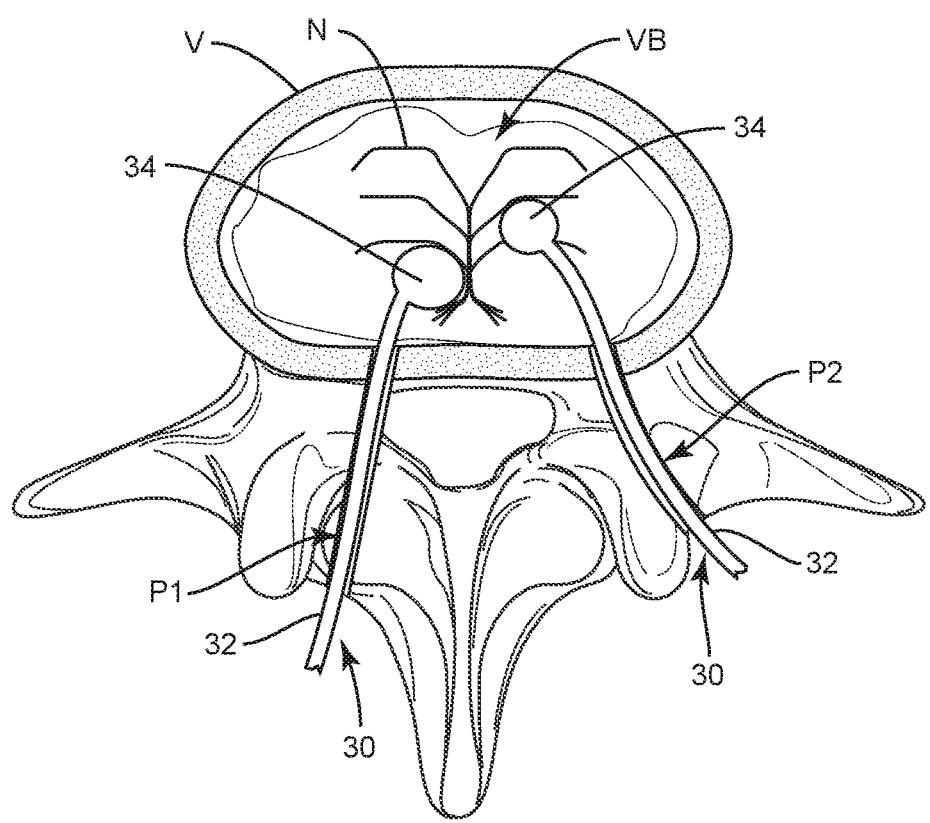
FIG. 4 is a top, cross sectional view of the vertebra shown in FIG. 3 with components of one of the balloon catheters discussed herein inserted into the vertebra.

Turning to FIGS. 2-4, in use, to treat the back and/or neck pain, such as, for example, chronic back and/or neck pain, a medical practitioner obtains access to a target location or treatment zone including at least one vertebra V that includes a nerve N, such as, for example, a basivertebral nerve in any appropriate manner, such as through incision and retraction of tissues. It is envisioned that the balloon catheter 30 may be used in any existing surgical method or technique including open surgery, mini-open surgery, minimally invasive surgery including percutaneous surgical implantation, whereby vertebra V is accessed through a micro-incision, or sleeve that provides a protected passageway to the area. Once access to the surgical site(s) are obtained, the particular surgical procedure is performed for treating back and/or neck pain.

In some embodiments, the medical practitioner may create a first pathway, such as, for example, pathway P1 to the target location/treatment zone, as shown in FIG. 2. In some embodiments, pathway P1 may include an opening O1 that extends through vertebra V and into a vertebral body VB of vertebra V to reach the target location/treatment zone, as also shown in FIG. 2. In some embodiments, pathway P1 is a straight path.

In some embodiments, the medical practitioner may create at least one additional pathway, such as, for example, a second pathway P2 to the target location/treatment zone. In some embodiments, pathway P2 may include an opening O2 that extends through vertebra V and into vertebral body VB to reach the target location/treatment zone, as shown in FIG. 2. In some embodiments, pathway P2 is a curved path.

In some embodiments, pathway P2 is created by the medical practitioner before or after pathway P1 is created by the medical practitioner. In some embodiments, pathway P2 is replaces pathway P1. That is, in some embodiments, pathway P2 created by the medical practitioner in addition to pathway P1 and in some embodiments, pathway P2 is the only pathway created by the medical practitioner.

Balloon catheter 30 may be moved along pathway P1 and/or pathway P2 such that balloon 34 moves through opening O1 and/or opening O2 and into vertebral body VB, as shown in FIG. 3. In some embodiments, balloon 34 is moved into vertebral body VB when balloon 34 is in the uninflated configuration, as shown in FIG. 3. In some embodiments, balloon 34 is moved into vertebral body VB when balloon 34 is in the uninflated configuration shown in FIG. 1. In some embodiments, balloon 34 is moved into vertebral body VB when balloon 34 is in the uninflated configuration shown in FIG. 1B. In some embodiments, pathways P1 and P2 and openings O1 and O2 each have a maximum width that is greater than that of balloon 34 when balloon 34 is in the uninflated configuration (FIGS. 1, 1B and/or 3) to avow balloon 34 to move easily through pathways P1 and P2 and openings O1 and O2 and into vertebral body VB to reach the target location/treatment zone. In some embodiments, the outer surface of balloon 34 is spaced apart from nerve N when balloon 34 is in the uninflated configuration, as shown in FIG. 3. In some embodiments, at least a portion of the outer surface of balloon 34 may contact at least a portion of nerve N when balloon 34 is in the uninflated configuration.

In some embodiments, the same balloon catheter 30 that is moved along pathway P1 is also moved along pathway P2. That is, balloon catheter 30 is moved in sequence such that balloon catheter 30 is first moved along one of pathways P1, P2 to move balloon 34 into vertebral body VB; balloon catheter 30 is removed from pathway P1 or P2; and balloon catheter 30 is then moved along the other one of pathways P1, P2 to move balloon 34 into vertebral body VB a second time. It is envisioned that this sequence may be repeated a number of times, as necessary. It is also envisioned that balloon catheter 30 can also be moved along pathways in addition to pathways P1, P2 that may be similar to or different from pathway P1 or pathway P2 to position balloon 34 within vertebral body VB in addition to moving balloon catheter 30 through pathways P1, P2. This allows one balloon catheter 30 to treat different areas of the treatment zone to effectively ablate and/or denervate nerve N.

In some embodiments, multiple balloon catheters 30 are provided such that a first balloon catheter 30 can be positioned within pathway P1 in the manner discussed above and a second balloon catheter 30 can be positioned within pathway P2 in the manner discussed above. It is envisioned that additional balloon catheters 30 may be positioned within pathways that may be similar to or different from pathway P1 or pathway P2 while the first and second balloon catheters 30 are positioned within pathways P1, P2. This allows a plurality of balloon catheters 30 to treat different areas of the treatment zone simultaneously to effectively ablate and/or denervate nerve N.

Once positioned within vertebral body VB, balloon 34 is moved from the uninflated configuration shown in FIGS. 1, 1B and/or 3 to the inflated configuration shown in FIG. 4. In particular, material may be moved through passageway 36 and into chamber 38 to move balloon 34 from the uninflated configuration to the inflated configuration, as discussed above. This allows balloon 34 to get as close as possible to the treatment zone. That is, the methods disclosed herein allow a chemical denervation agent, such as, for example, one or more of the chemical denervation agents discussed herein to get as close as possible to a nerve, such as, for example, a basivertebral nerve so that the chemical denervation agent can effectively ablate and/or denervate the nerve.

In some embodiments, the material moved through passageway 36 and into chamber 38 to move balloon 34 from the uninflated configuration to the inflated configuration is a conventional inflation material, such as, for example, air or saline. At least a portion of the outer surface of the porous balloon 34 is coated with a chemical denervation agent, such as, for example, at least one of the chemical denervation agents discussed herein, and at least a portion of the outer surface of balloon 34 contacts at least a portion of nerve N when balloon 34 is in the inflated configuration, as shown in FIG. 4. When the outer surface of balloon 34 contacts at least a portion of nerve N, the chemical denervation agent that coats at least a portion of the outer surface of balloon 34 ablates and/or denervates nerve N, thus reducing back and/or neck pain in the patient. In some embodiments, the outer surface of balloon 34 is spaced apart from nerve N when balloon 34 is in the inflated configuration and the chemical denervation agent that coats balloon 34 diffuses within vertebral body VB to reach nerve N. In some embodiments, the balloon 34 that is filled with the conventional inflation material is a porous balloon. In some embodiments, the balloon 34 that is filled with the conventional inflation material is a non-porous balloon. In some embodiments, the conventional inflation material is free of any chemical denervation agent or therapeutic agent, such as, for example, the chemical denervation agents or therapeutic agents discussed herein. In some embodiments, the conventional inflation material consists of air. In some embodiments, the conventional inflation material consists of saline.

In some embodiments, the material moved through passageway 36 and into chamber 38 to move balloon 34 from the uninflated configuration to the inflated configuration is a chemical denervation agent, such as, for example, one or more of the chemical denervation agents discussed herein, and balloon 34 comprises a porous material. That is, balloon 34 is a porous balloon that is at least partially filled with the chemical denervation agent such that when balloon 34 is positioned at, in or near the treatment zone, the chemical denervation agent is released from balloon 34 so as to ablate and/or denervate nerve N, thus reducing back and/or neck pain in the patient. In some embodiments, this configuration prolongs the release of the chemical denervation agent. That is, the chemical denervation agent is released from balloon 34 over time, rather than all at once. In some embodiments, porous balloon 34 delivers the chemical denervation agent so that the chemical denervation agent directly contacts nerve N.

In some embodiments, porous balloon 34 delivers the chemical denervation agent so that the chemical denervation agent within about 0.05 mm to about 5 mm of nerve N. In some embodiments, porous balloon 34 delivers the chemical denervation agent so that the chemical denervation agent within about 1 mm of nerve N. It is envisioned that at least in some embodiments, the chemical denervation agent will migrate from the delivery site to contact nerve N. In some embodiments, the porous balloon 34 is configured such that the chemical denervation agent will not move through pores of the porous balloon 34 until the pressure within chamber 38 reaches a pre-determined threshold. For example, the chemical denervation agent may be moved through passageway 36 and into chamber 38 using a first pressure to move balloon 34 from the uninflated configuration to the inflated configuration. As such, when balloon 34 is in the inflated configuration, the pressure within chamber 38 will be the same or approximately the same as the first pressure. When the pressure within chamber 38 is the same or approximately the same as the first pressure, the chemical denervation agent is prevented from moving through pores of balloon 34. Additional amounts of the chemical denervation agent and/or another material may then be moved through passageway 36 and into chamber 38 to further inflate balloon 34, which will increase the pressure within chamber 38 to a second pressure that is greater than the first pressure. When the pressure within chamber 38 is the same or approximately the same as the second pressure, the chemical denervation agent is able to move through pores of balloon 34 and either directly contact nerve N or migrate to nerve N.

In some embodiments, at least a portion of the outer surface of the porous balloon 34 is coated with a chemical denervation agent, such as, for example, at least one of the chemical denervation agents discussed herein, and at least a portion of the outer surface of balloon 34 contacts at least a portion of nerve N when balloon 34 is in the inflated configuration, as shown in FIG. 4. When the outer surface of balloon 34 contacts at least a portion of nerve N, the chemical denervation agent that coats at least a portion of the outer surface of balloon 34 ablates and/or denervates nerve N, thus reducing back and/or neck pain in the patient.

In some embodiments, the material moved through passageway 36 and into chamber 38 to move balloon 34 from the uninflated configuration to the inflated configuration is a chemical denervation agent, such as, for example, one or more of the chemical denervation agents discussed herein, and balloon 34 comprises a biodegradable and/or bioresorbable material. That is, balloon 34 is a biodegradable and/or bioresorbable balloon that is at least partially filled with the chemical denervation agent such that when balloon 34 is positioned at, in or near the treatment zone, as balloon 34 degrades and/or resorbs, the chemical denervation agent is released from balloon 34 so as to ablate and/or denervate nerve N, thus reducing back and/or neck pain in the patient.

Figure 5:
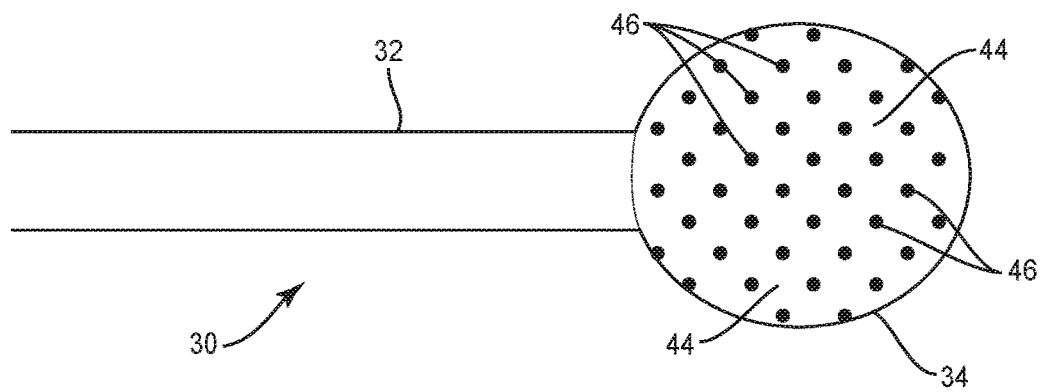
FIG. 5 is a side view of components of one embodiment of a balloon catheter in accordance with the principles of the present disclosure.
Figure 6:
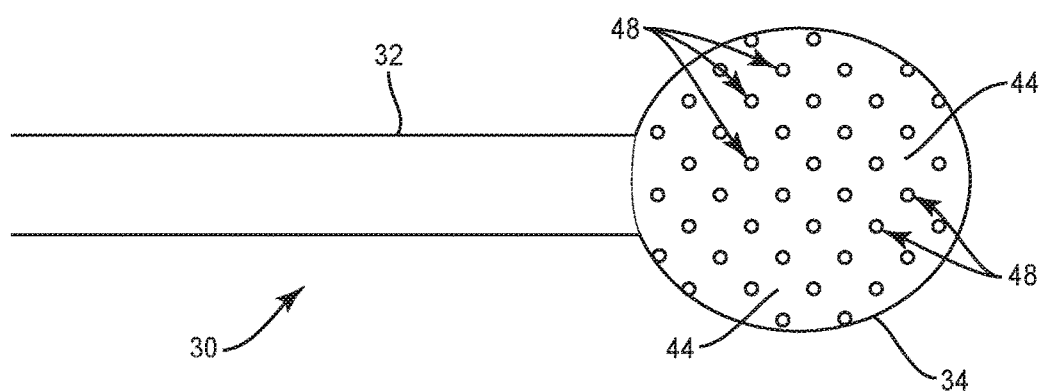
FIG. 6 is a side view of the balloon catheter shown in FIG. 5.

In some embodiments, shown in FIGS. 5 and 6, the material moved through passageway 36 and into chamber 38 to move balloon 34 from the uninflated configuration to the inflated configuration is a chemical denervation agent, such as, for example, one or more of the chemical denervation agents discussed herein, and balloon 34 comprises a first material 44 and a second material 46 that is different than first material 44, as shown in FIG. 5. In some embodiments, first material 44 is a biocompatible material that is not biodegradable or bioresorbable material and second material 46 is a biocompatible material that is biodegradable and/or bioresorbable. In some embodiments, first material 44 is a biocompatible material that is biodegradable and/or bioresorbable material and second material 46 is a biocompatible material that is biodegradable and/or bioresorbable, wherein first material 44 degrades or is resorbed at a first rate and second material degrades or is resorbed at a second rate that is faster than the first rate. As such, as second material 46 degrades or is resorbed, first material 44 remains such that the degradation or resorption of second material 46 forms pores, such as, for example, holes 48 in balloon 34, as shown in FIG. 6. As holes 48 form by the degradation and/or resorption of second material 46, the chemical denervation agent will seep out of holes 48 so as to ablate and/or denervate nerve N, thus reducing back and/or neck pain in the patient. In some embodiments, second material 46 degrades to form holes 48 within 1 hour to 1 week following implantation of balloon 34. In some embodiments, second material 46 degrades to form holes 48 within 1 day to 7 days following implantation of balloon 34. In some embodiments, second material 46 degrades to form holes 48 within 24 hours to 48 hours following implantation of balloon 34. In some embodiments, second material 46 degrades to form holes 48 within 24 hours following implantation of balloon 34.

It is envisioned that balloon 34 may be moved into vertebral body when balloon 34 is in the inflated configuration. That is, after the medical practitioner creates pathway P1 and/or pathway P2, material may be moved through passageway 36 and into chamber 38 to move balloon 34 from the uninflated configuration to the inflated configuration, as discussed above, before balloon 34 is moved through pathway P1 and/or pathway P2 and into vertebral body VB. It is envisioned that inflating balloon 34 prior to moving balloon 34 through pathway P1 and/or pathway P2 and into vertebral body VB may reduce or prevent physical and/or psychological trauma to the patient.

Figure 7:
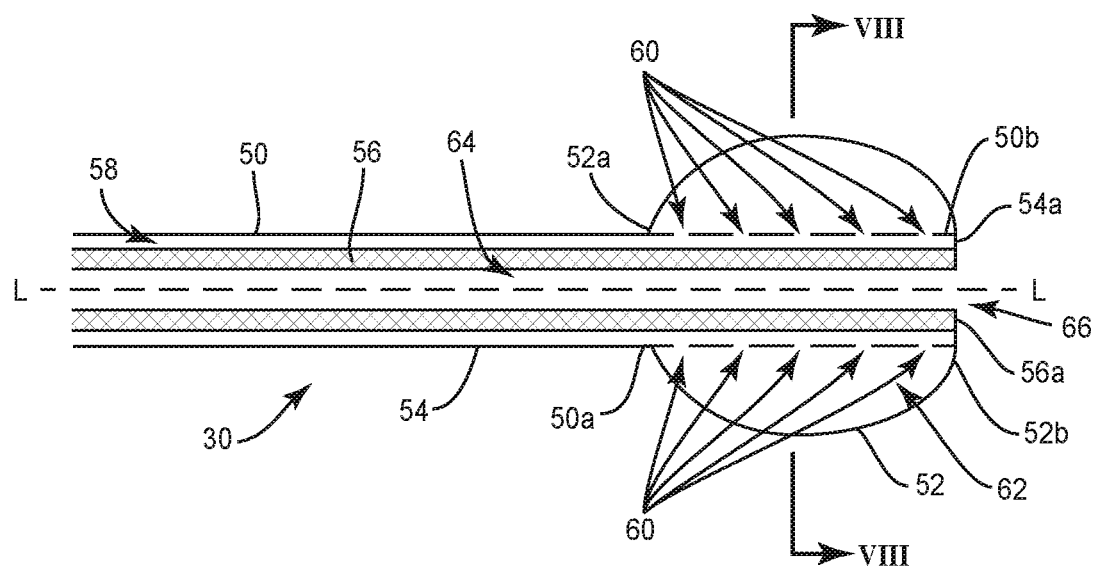
FIG. 7 is a side, cross sectional view of components of one embodiment of a balloon catheter in accordance with the principles of the present disclosure.
Figure 8:
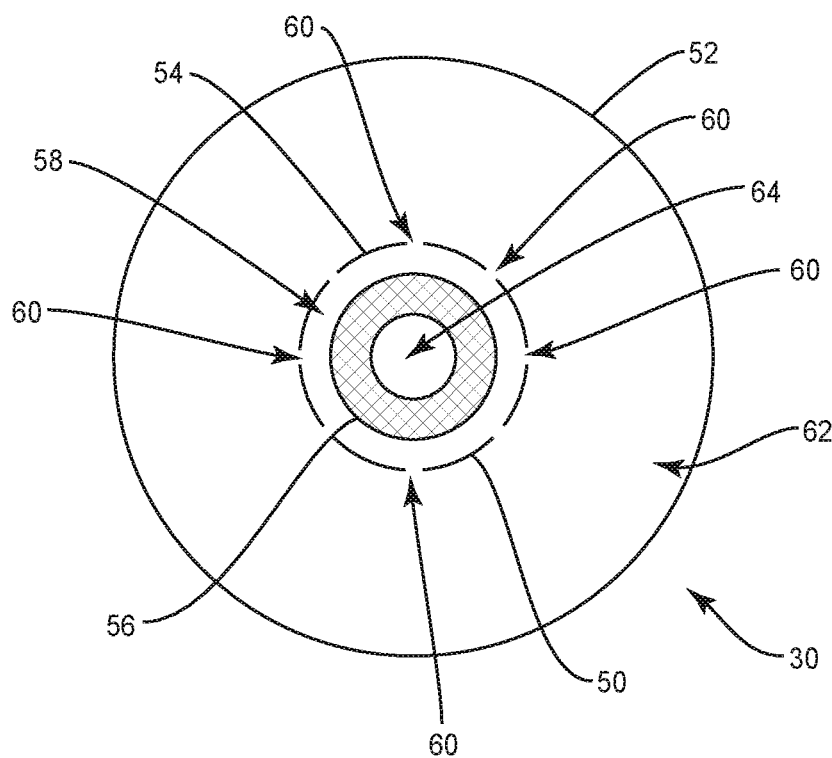
FIG. 8 is a cross sectional view of the balloon catheter shown in FIG. 7 taken along lines VIII-VIII in FIG. 7.

In one embodiment, shown in FIGS. 7 and 8, balloon catheter 30 includes a cylindrical portion 50 and a balloon 52 coupled to cylindrical portion 50. Cylindrical portion 50 extends through balloon 52, as shown in FIG. 7. That is, a first end 52a of balloon 52 is coupled to a first section 50a of cylindrical portion 50 and an opposite second end 52b of balloon is coupled to a second section 50b of cylindrical portion 50. Cylindrical portion 50 comprises an outer shaft 54 and an inner shaft 56 positioned within outer shaft 54. In some embodiments, inner shaft 56 is coaxial and/or concentric with outer shaft 54. Inner shaft 56 is spaced apart from outer shaft 54 such that a space between inner shaft 56 and outer shaft 54 defines a first lumen 58. That is, the space defined by an outer surface of inner shaft 56 and an inner surface of outer shaft 54 defines first lumen 58. A distal end of outer shaft 54 comprises one or a plurality of openings 60 that are in communication with an internal chamber 62 of balloon 52 such that a material that is injected into first lumen 58 will enter chamber 62 through openings 60 to move balloon 52 from an unexpanded configuration, such as, for example, an uninflated configuration (FIG. 8A) to an expanded configuration, such as, for example, an inflated configuration (FIG. 8B). That is, a material may be moved through first lumen 58 and openings 60 and into chamber 62 to move balloon 52 from the uninflated configuration to the inflated configuration. When balloon 52 is in the inflated configuration, balloon 52 has a maximum diameter that is greater than the maximum diameter of balloon 52 when balloon 52 is in the uninflated configuration. In some embodiments, outer shaft 54 comprises a plurality of openings 60 that are spaced apart from one another longitudinally along a longitudinal axis L defined by outer shaft 54, as shown in FIG. 7. In some embodiments, outer shaft 54 comprises a plurality of openings 60 that are spaced apart from one another radially about a circumference of outer shaft 54, as shown in FIG. 8.

In some embodiments, first lumen 58 may be disposed at alternate orientations, relative to longitudinal axis L, such as, for example, parallel, transverse and/or other angular orientations such as acute or obtuse, co-axial and/or may be offset or staggered. In some embodiments, first lumen 58 may have various cross section configurations, such as, for example, oval, oblong, triangular, rectangular, square, polygonal, irregular, uniform, non-uniform, variable, tubular and/or tapered. In some embodiments, openings 60 can have various shape configurations, such as, for example, circular, oval, oblong, polygonal, irregular, uniform, non-uniform, variable and/or tapered. In some embodiments, openings 60 may be disposed at alternate orientations, relative to longitudinal axis L, such as, for example, transverse, perpendicular and/or other angular orientations such as acute or obtuse, co-axial and/or may be offset or staggered. In some embodiments, the material that is used to inflate balloon 52 is a chemical denervation agent, such as, for example, one or more of the chemical denervation agents discussed herein. In some embodiments, the material that is used to inflate balloon 52 is a gas, such as, for example, air. In some embodiments, the material is a liquid, such as, for example, saline or water. In some embodiments, outer shaft 54 comprises an end surface 54a that closes off first lumen 58 such that the material that is used to move balloon 52 from the uninflated configuration to the inflated configuration remains within first lumen 58 and/or chamber 62, and does not escape through end surface 54a. In some embodiments, balloon 52 may the same or similar to balloon 34 and may be made of the same or similar materials and/or have the same or similar characteristics as those discussed above with regard to balloon 34.

In some embodiments, inner shaft 56 is hollow and defines a second lumen 64 that is spaced apart from first lumen 58 by inner shaft 56. In some embodiments, second lumen 64 is not in communication with first lumen 58. Second lumen 64 comprises an aperture 66 that extends through a distal end surface 56a of inner shaft 56. In some embodiments, a guide wire, such as, for example, a K-wire, may be positioned through second lumen 64 such that the guide wire extends through aperture 66 and into tissue, for example, to allow a medical practitioner to guide balloon catheter 30 to a target location along the guide wire. In some embodiments, a material, such as, for example, a chemical denervation agent, such as, for example, one or more of the chemical denervation agents discussed herein may be inserted into inner shaft 56 such that the material moves through second lumen 64 and out of aperture 66 to deliver the material to a target location, such as, for example, a location within vertebral body VB. In some embodiments, second lumen 64 may be disposed at alternate orientations, relative to longitudinal axis L and/or first lumen 58, such as, for example, parallel, transverse and/or other angular orientations such as acute or obtuse, co-axial and/or may be offset or staggered. In some embodiments, second lumen 64 may have various cross section configurations, such as, for example, oval, oblong, triangular, rectangular, square, polygonal, irregular, uniform, non-uniform, variable, tubular and/or tapered.

In some embodiments, outer shaft 54 and/or inner shaft 56 is flexible to allow cylindrical portion 50 to bend as cylindrical portion 50 is navigated through a patient's anatomy. For example, cylindrical portion 50 may be flexible to allow cylindrical portion 50 to be navigated along a curved path created by a medical practitioner in order to position balloon 52 at, in or near a target location or treatment zone, such as, for example, a basivertebral nerve. In embodiments wherein cylindrical portion 50 is flexible, cylindrical portion 50 can be bent without breaking cylindrical portion 50. In some embodiments, outer shaft 54 and/or inner shaft 56 is rigid such that cylindrical portion 50 cannot be bent without cylindrical portion 50 breaking. For example, cylindrical portion 50 may be rigid to provide strength to cylindrical portion 50 in applications wherein balloon catheter 30 is navigated along a straight path created by a medical practitioner in order to position balloon 52 at, in or near a target location or treatment zone, such as, for example, a basivertebral nerve.

Figure 8A:
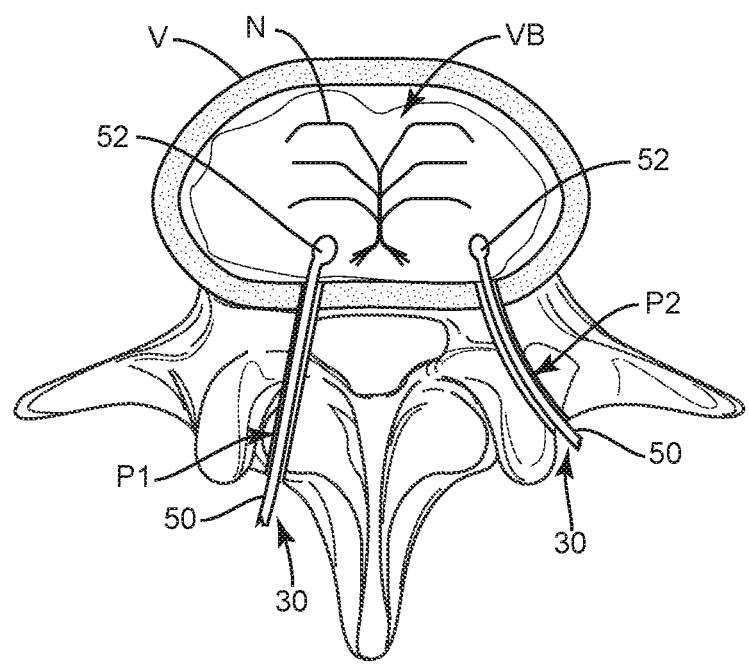
FIG. 8A is a top, cross sectional view of the vertebra shown in FIG. 3 with components of one of the balloon catheters discussed herein inserted into the vertebra.
Figure 8B:
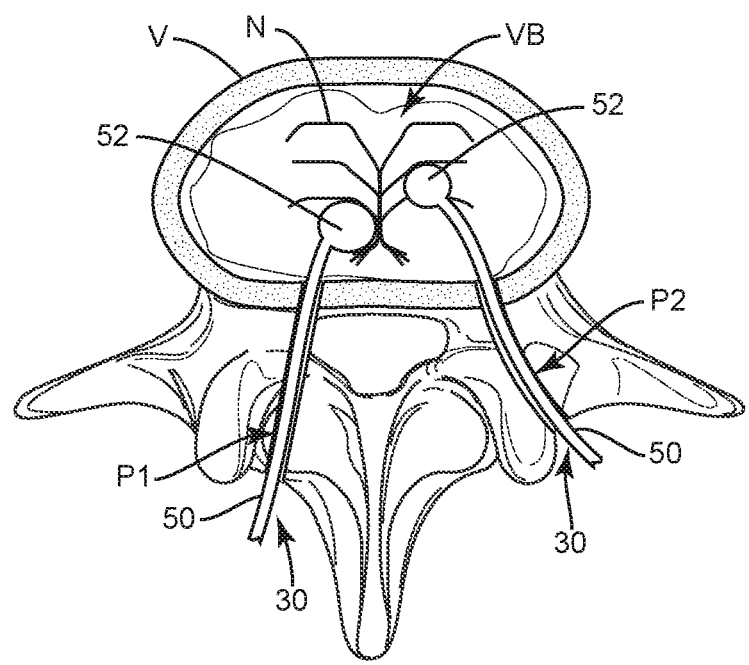
FIG. 8B is a top, cross sectional view of the vertebra shown in FIG. 3 with components of one of the balloon catheters discussed herein inserted into the vertebra.

Referring to FIGS. 8A and 8B, in use, balloon catheter 30 may be moved along pathway P1 and/or pathway P2 such that balloon 52 moves through opening O1 and/or opening O2 and into vertebral body VB, as shown in FIG. 8A. In some embodiments, a guide wire, such as, for example, a K-wire, may be positioned through second lumen 64 such that the guide wire extends through aperture 66 and into tissue, such as, for example, vertebral body VB to allow a medical practitioner to guide balloon catheter 30 into vertebral body VB. In some embodiments, balloon 52 is moved into vertebral body VB when balloon 52 is in the uninflated configuration, as shown in FIG. 8A. In some embodiments, pathways P1 and P2 and openings O1 and O2 each have a maximum width that is greater than that of balloon 52 when balloon 52 is in the uninflated configuration to allow balloon 52 to move easily through pathways P1 and P2 and openings O1 and O2 and into vertebral body VB to reach the target location/treatment zone. In some embodiments, the outer surface of balloon 52 is spaced apart from nerve N when balloon 52 is in the uninflated configuration, as shown in FIG. 8A. In some embodiments, at least a portion of the outer surface of balloon 52 may contact at least a portion of nerve N when balloon 52 is in the uninflated configuration. In embodiments wherein a chemical denervation agent is used to inflate balloon 52, balloon 52 may comprise a porous material to avow the chemical denervation agent to exit balloon 52 through pores, as discussed with regard to balloon 34, when balloon 34 comprises a porous material.

Once positioned within vertebral body VB, balloon 52 is moved from the uninflated configuration (FIG. 8A) to the inflated configuration (FIG. 8B). In particular, material may be moved through first lumen 58 and into chamber 62 through openings 60 to move balloon 34 from the uninflated configuration to the inflated configuration, as discussed above. This allows balloon 52 to get as close as possible to the treatment zone. In some embodiments, the material that is moved first lumen 58 and into chamber 62 through openings 60 to move balloon 52 from the uninflated configuration to the inflated configuration is a conventional inflation material, such as, for example, one or more of the conventional inflation materials discussed herein. In some embodiments, the material that is moved through first lumen 58 and into chamber 62 through openings 60 to move balloon 52 from the uninflated configuration to the inflated configuration is a chemical denervation agent, such as, for example, one or more of the chemical denervation agents discussed herein.

A chemical denervation agent, such as, for example, one or more of the chemical denervation agents discussed herein, is moved through second lumen 64 and aperture 66 to deliver the chemical denervation agent at, in or near nerve N such that the chemical denervation agent ablates and/or denervates nerve N, thus reducing back and/or neck pain in the patient. In some embodiments, the chemical denervation agent is moved through second lumen 64 and aperture 66 to deliver the chemical denervation agent at, in or near nerve N before balloon 52 is moved from the uninflated configuration (FIG. 8A) to the inflated configuration (FIG. 8B). That is, the chemical denervation agent is moved through second lumen 64 and aperture 66 when balloon is in the uninflated configuration. In some embodiments, the chemical denervation agent is moved through second lumen 64 and aperture 66 to deliver the chemical denervation agent at, in or near nerve N after balloon 52 is moved from the uninflated configuration (FIG. 8A) to the inflated configuration (FIG. 8B). That is, the chemical denervation agent is moved through second lumen 64 and aperture 66 when balloon is in the inflated configuration.

Figure 9:
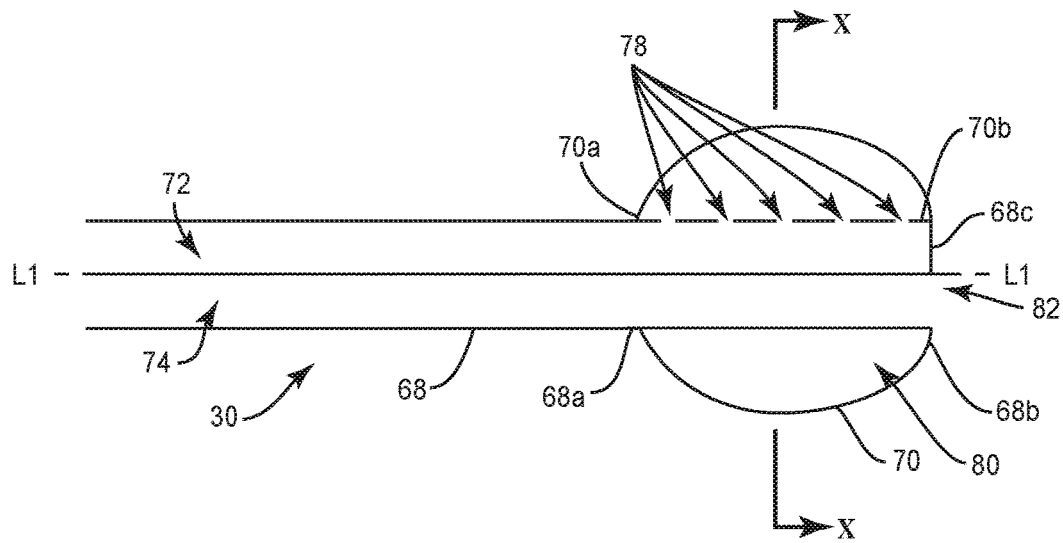
FIG. 9 is a side, cross sectional view of components of one embodiment of a balloon catheter in accordance with the principles of the present disclosure.
Figure 10:
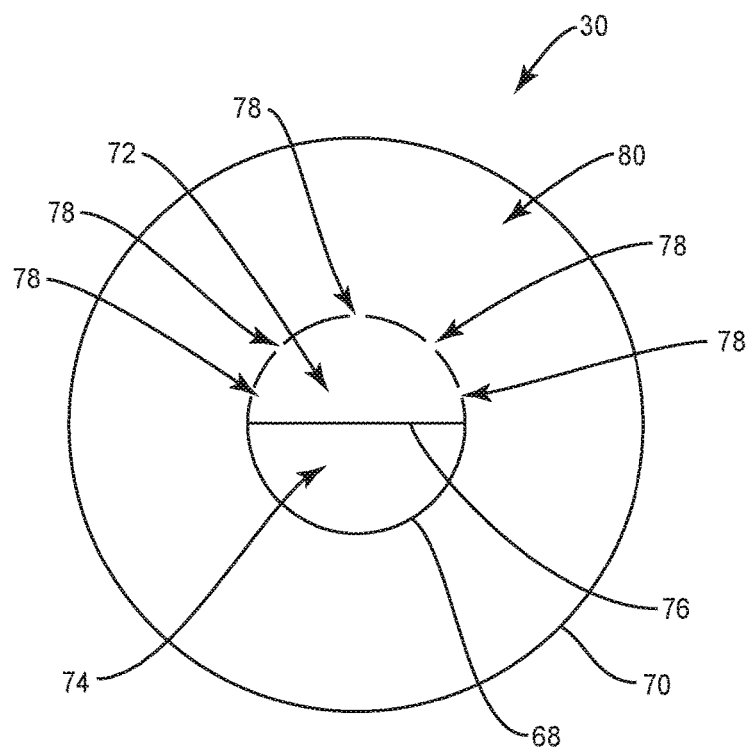
FIG. 10 is a cross sectional view of the balloon catheter shown in FIG. 9 taken along lines X-X in FIG. 9.

In one embodiment, shown in FIGS. 9 and 10, balloon catheter 30 includes a cylindrical portion 68 and a balloon 70 coupled to cylindrical portion 68. Cylindrical portion 68 extends through balloon 70, as shown in FIG. 9. That is, a first end 70a of balloon 70 is coupled to a first section 68a of cylindrical portion 68 and an opposite second end 70b of balloon is coupled to a second section 68h of cylindrical portion 68. Cylindrical portion 68 comprises a first lumen 72 and a second lumen 74 that is spaced apart from first lumen 72 by a wall 76 that extends the entire length of cylindrical portion 68. First lumen 72 is parallel to second lumen 74. First and second lumens 72, 74 are disposed side-by-side. That is, first lumen 72 is not coaxial and/or concentric with second lumen 74. In some embodiments, wall 76 divides cylindrical portion 68 such that first lumen 72 is the same size as second lumen 74. In some embodiments, wall 76 divides cylindrical portion 68 such that first lumen 72 has a larger cross section than second lumen 74. In some embodiments, wall 76 divides cylindrical portion 68 such that first lumen 72 has a smaller cross section than second lumen 74.

Figure 10A:
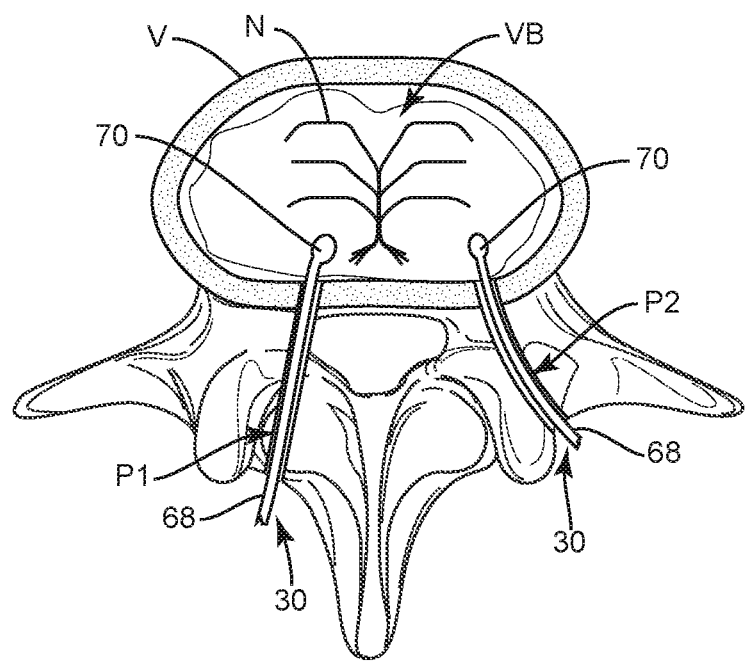
FIG. 10A is a top, cross sectional view of the vertebra shown in FIG. 3 with components of one of the balloon catheters discussed herein inserted into the vertebra.
Figure 10B:
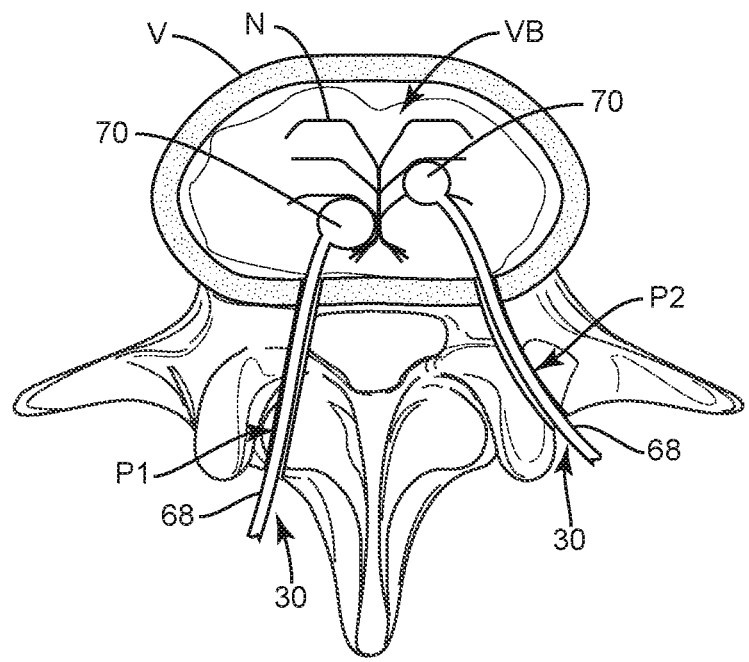
FIG. 10B is a top, cross sectional view of the vertebra shown in FIG. 3 with components of one of the balloon catheters discussed herein inserted into the vertebra.

A distal end of cylindrical portion 68 comprises one or a plurality of openings 78 that are in communication with an internal chamber 80 of balloon 70 such that a material that is injected into first lumen 72 will enter chamber 80 through openings 78 to move balloon 70 from an unexpanded configuration, such as, for example, an uninflated configuration (FIG. 10A) to an expanded configuration, such as, for example, an inflated configuration (FIG. 10B). That is, a material may be moved through first lumen 72 and openings 78 and into chamber 80 to move balloon 70 from the uninflated configuration to the inflated configuration. When balloon 70 is in the inflated configuration, balloon 70 has a maximum diameter that is greater than the maximum diameter of balloon 70 when balloon 70 is in the uninflated configuration. In some embodiments, openings 78 are spaced apart from one another longitudinally along a longitudinal axis L1 defined by cylindrical portion 68, as shown in FIG. 9. In some embodiments, openings 78 are spaced apart from one another radially about a circumference of cylindrical portion 68, as shown in FIG. 10.

In some embodiments, first lumen 72 and/or second lumen 74 may be disposed at alternate orientations, relative to longitudinal axis L1, such as, for example, parallel, transverse and/or other angular orientations such as acute or obtuse, co-axial and/or may be offset or staggered. In some embodiments, first lumen 72 and/or second lumen 74 may have various cross section configurations, such as, for example, half-moon, oval, oblong, triangular, rectangular, square, polygonal, irregular, uniform, non-uniform, variable, tubular and/or tapered. In some embodiments, openings 78 can have various shape configurations, such as, for example, circular, oval, oblong, polygonal, irregular, uniform, non-uniform, variable and/or tapered. In some embodiments, openings 78 may be disposed at alternate orientations, to longitudinal axis L1, such as, for example, transverse, perpendicular and/or other angular orientations such as acute or obtuse, co-axial and/or may be offset or staggered. In some embodiments, the material that is used to inflate balloon 70 is a chemical denervation agent, such as, for example, at least one of the chemical denervation agents discussed above. In some embodiments, the material that is used to inflate balloon 70 is a gas, such as, for example, air. In some embodiments, the material is a liquid, such as, for example, saline or water. In some embodiments, cylindrical portion 68 comprises an end surface 68c that closes off first lumen 72 such that the material that is used to move balloon 70 from the uninflated configuration to the inflated configuration remains within first lumen 72 and/or chamber 80, and does not escape through end surface 68c. In some embodiments, balloon 70 may the same or similar to balloon 34 and/or balloon 52 and may be made of the same or similar materials and/or have the same or similar characteristics as those discussed above with regard to balloon 34 and/or balloon 52.

In some embodiments, second lumen 74 is not in communication with first lumen 72. Second lumen 74 comprises an aperture 82 that extends through end surface 68c. In some embodiments, a guide wire, such as, for example, a K-wire, may be positioned through second lumen 74 such that the guide wire extends through aperture 82 and into tissue, for example, to allow a medical practitioner to guide balloon catheter 30 to a target location along the guide wire. In some embodiments, a material, such as, for example, a chemical denervation agent, such as, for example, one or more of the chemical denervation agents discussed above, may be inserted into second lumen 74 such that the material moves through second lumen 74 and out of aperture 82 to deliver the material to a target location, such as, for example, vertebral body VB.

In some embodiments, cylindrical portion 68 is flexible to allow cylindrical portion 68 to bend as cylindrical portion 68 is navigated through a patient's anatomy. For example, cylindrical portion 68 may be flexible to allow cylindrical portion 68 to be navigated along a curved path created by a medical practitioner in order to position balloon 70 at, in or near a target location or treatment zone, such as, for example, a basivertebral nerve. In embodiments wherein cylindrical portion 68 is flexible, cylindrical portion 68 can be bent without breaking cylindrical portion 68. In some embodiments, cylindrical portion 68 is rigid such that cylindrical portion 68 cannot be bent without cylindrical portion 68 breaking. For example, cylindrical portion 68 may be rigid to provide strength to cylindrical portion 68 in applications wherein balloon catheter 30 is navigated along a straight path created by a medical practitioner in order to position balloon 70 at, in or near a target location or treatment zone, such as, for example, a basivertebral nerve.

Referring to FIGS. 10A and 10B, in use, balloon catheter 30 may be moved along pathway P1 and/or pathway P2 such that balloon 52 moves through opening O1 and/or opening O2 and into vertebral body VB, as shown in FIG. 10A. In some embodiments, a guide wire, such as, for example, a K-wire, may be positioned through second lumen 74 such that the guide wire extends through aperture 82 and into tissue, such as, for example, vertebral body VB to avow a medical practitioner to guide balloon catheter 30 into vertebral body VB. In some embodiments, balloon 70 is moved into vertebral body VB when balloon 70 is in the uninflated configuration, as shown in FIG. 10A. In some embodiments, pathways P1 and P2 and openings O1 and O2 each have a maximum width that is greater than that of balloon 70 when balloon 70 is in the uninflated configuration to allow balloon 70 to move easily through pathways P1 and P2 and openings O1 and O2 and into vertebral body VB to reach the target location/treatment zone. In some embodiments, the outer surface of balloon 70 is spaced apart from nerve N when balloon 70 is in the uninflated configuration, as shown in FIG. 10A. In some embodiments, at least a portion of the outer surface of balloon 70 may contact at least a portion of nerve N when balloon 70 is in the uninflated configuration.

Once positioned within vertebral body VB, balloon 70 is moved from the uninflated configuration (FIG. 10A) to the inflated configuration (FIG. 10B). In particular, material may be moved through first lumen 70 and into chamber 80 through openings 78 to move balloon 70 from the uninflated configuration to the inflated configuration, as discussed above. This allows balloon 70 to get as close as possible to the treatment zone. In some embodiments, the material that is moved through first lumen 70 and into chamber 80 through openings 78 to move balloon 70 from the uninflated configuration to the inflated configuration is a conventional inflation material, such as, for example, one or more of the conventional inflation materials discussed herein. In some embodiments, the material that is moved through first lumen 70 and into chamber 80 through openings 78 to move balloon 70 from the uninflated configuration to the inflated configuration is a chemical denervation agent, such as, for example, one or more of the chemical denervation agents discussed herein. In embodiments wherein a chemical denervation agent is used to inflate balloon 70, balloon 70 may comprise a porous material such that the chemical denervation agent will exit balloon 70 through pores in balloon 70 in the same manner or a similar manner as discussed above with regard to balloon 34.

A chemical denervation agent, such as, for example, one or more of the chemical denervation agents discussed herein, is moved through second lumen 74 and aperture 82 to deliver the chemical denervation agent at, in or near nerve N such that the chemical denervation agent ablates and/or denervates nerve N, thus reducing back and/or neck pain in the patient. In some embodiments, the chemical denervation agent is moved through second lumen 74 and aperture 82 to deliver the chemical denervation agent at, in or near nerve N before balloon 70 is moved from the uninflated configuration (FIG. 10A) to the inflated configuration (FIG. 10B). That is, the chemical denervation agent is moved through second lumen 74 and aperture 82 when balloon is in the uninflated configuration. In some embodiments, the chemical denervation agent is moved through second lumen 74 and aperture 82 to deliver the chemical denervation agent at, in or near nerve N after balloon 70 is moved from the uninflated configuration (FIG. 10A) to the inflated configuration (FIG. 10B). That is, the chemical denervation agent is moved through second lumen 74 and aperture 70 when balloon is in the inflated configuration.

In some embodiments, at least a portion of balloon catheter 30 is flexible and balloon catheter 30 is steerable. That is, balloon catheter 30 can be actively steered through the anatomy of a patient, such as, for example, along pathway P1 and/or pathway P2, such that the medical practitioner can bend balloon catheter 30 in a controlled manner from an area outside the patient, while at least a balloon of balloon catheter 30 is positioned within the patient, to better navigate balloon catheter 30 through the patient's anatomy. It is envisioned that steerable balloon catheters 30 may be particularly useful when the pathway balloon catheter 30 needs to travel along is not straight. Steerable balloon catheters 30 are also useful to steer around portions of the patient's anatomy the medical practitioner wishes to avoid contacting, such as, for example, portions of the patient's anatomy that would cause trauma or injury to the patient if contacted with balloon catheter 30.

Figure 11:
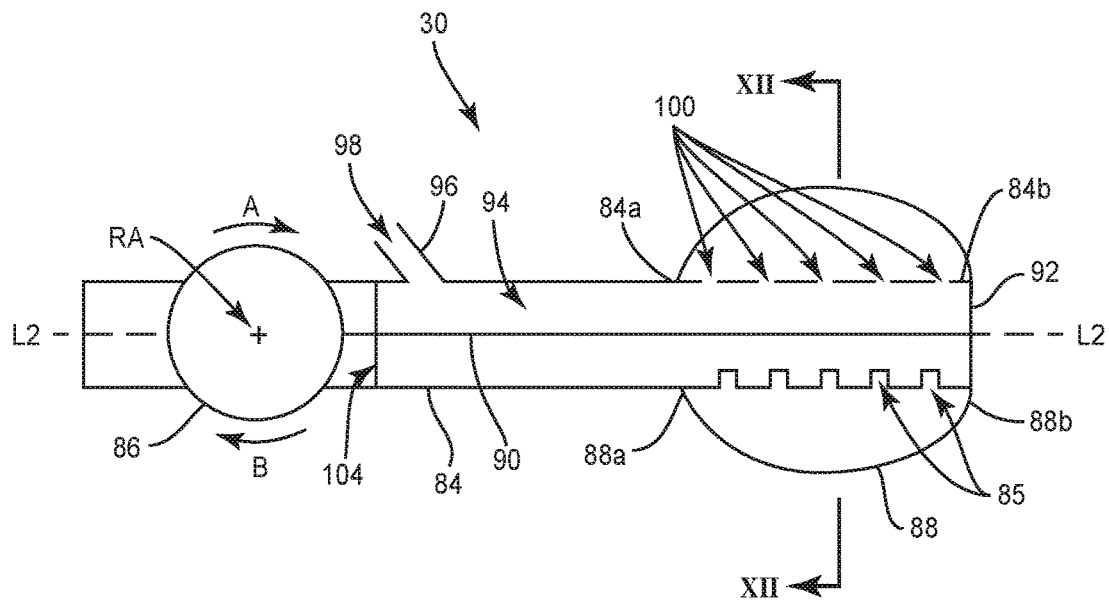
FIG. 11 is a side, cross sectional view of components of one embodiment of a balloon catheter in accordance with the principles of the present disclosure.
Figure 11A:
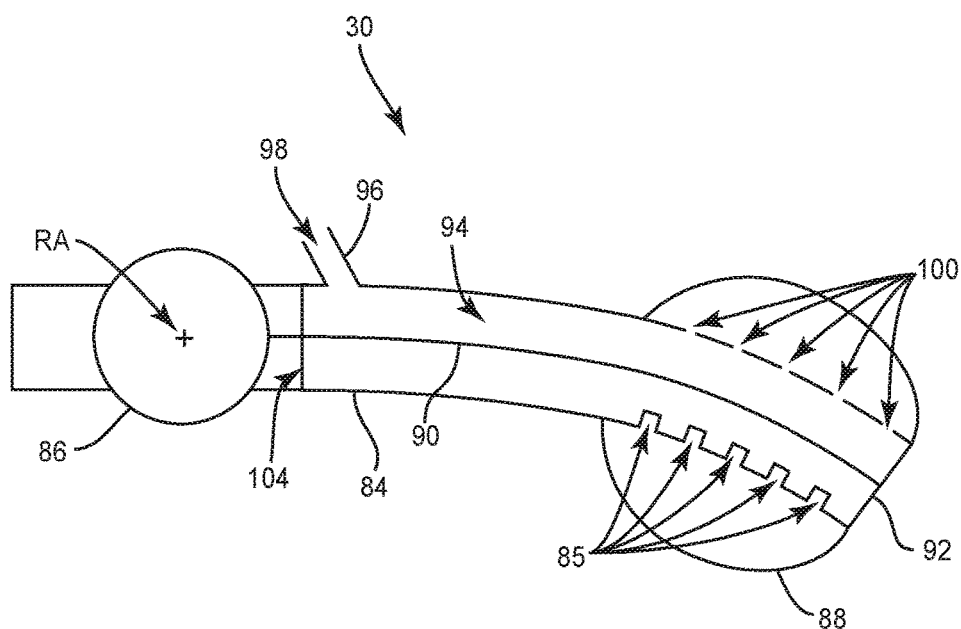
FIG. 11A is a side, cross sectional view of the balloon catheter shown in FIG. 11.
Figure 12:
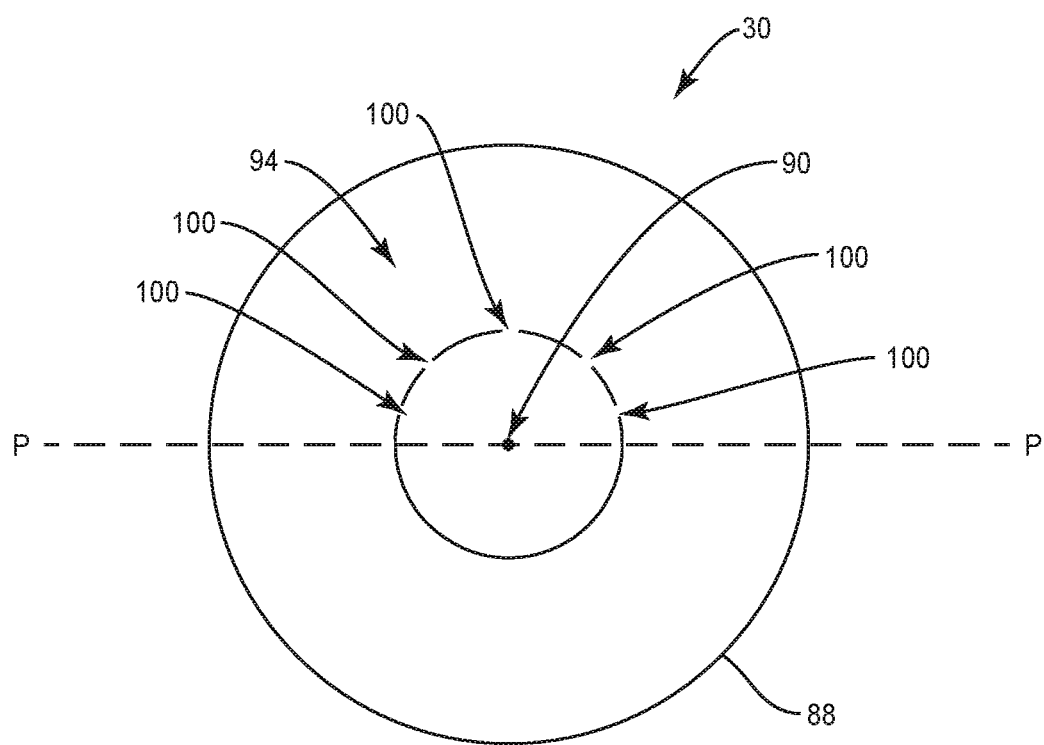
FIG. 12 is a cross sectional view of the balloon catheter shown in FIG. 11 taken along lines XII-XII in FIG. 11.

In one embodiment, shown in FIGS. 11, 11A and 12, balloon catheter 30 is steerable and includes a cylindrical portion 84. Cylindrical portion 84 comprises a spool 86 rotatably coupled to a proximal end of cylindrical portion 84 and a balloon 88 coupled to a distal end of cylindrical portion 84. Spool 86 is rotatable about a rotation axis RA in a first direction, such as, for example, the direction shown by arrow A in FIG. 11 and an opposite second direction, such as, for example, the direction shown by arrow B in FIG. 11. A first end of a cable 90 is wound about spool 86 and a second end of cable 90 is fixed to a distal end wall 92 of cylindrical portion 84. Rotating spool 86 relative to cylindrical portion 84 about rotation axis RA in one direction, such as, for example, direction A or B, will cause more cable 90 to wind about spool 86, thus causing the distal end of cylindrical portion 84 to bend. Rotating spool 86 relative to cylindrical portion 84 about rotation axis RA in another direction, such as, for example, direction A or B, will cause more cable 90 to unwind from spool 86, thus causing the distal end of cylindrical portion 84 to straighten. For example, balloon catheter 30 is movable between a first configuration, shown in FIG. 11, in which cylindrical portion 84 is straight, and a second configuration, shown in FIG. 11A, in which cylindrical portion 84 is bent. As discussed above, balloon catheter 30 is movable between the first and second configurations by rotating spool 86 to wind and unwind cable 90. In some embodiments, the distal end of cylindrical portion 84 comprises one or a plurality of notches 85 configured to facilitate bending of cylindrical portion 84. That is, notches 85 will help cylindrical portion 84 bend to move balloon catheter 30 from the first configuration to the second configuration. Cylindrical portion 84 is flexible to avow cylindrical portion 84 to bend as cylindrical portion 84 moves from the first configuration to the second configuration and is navigated through a patient's anatomy. In some embodiments, cylindrical portion 84 comprises a memory material, such as, for example, nitinol, to help cylindrical portion 84 return to the first configuration from the second configuration.

Cylindrical portion 84 extends through balloon 88, as shown in FIGS. 11 and 11A. That is, a first end 88a of balloon 88 is coupled to a first section 84a of cylindrical portion 84 and an opposite second end 88b of balloon 88 is coupled to a second section 84b of cylindrical portion 84. Cylindrical portion 84 comprises a lumen 94 and a port 96 that is in communication with lumen 94. Port 96 includes an aperture 98. The distal end of cylindrical portion 84 comprises one or a plurality of openings 100 that are in communication with an internal chamber 102 of balloon 88 such that a material that is injected through aperture 98 and into lumen 94 will enter chamber 102 through openings 100 to move balloon 88 from an unexpanded configuration, such as, for example, an uninflated configuration (FIG. 12A) to an expanded configuration, such as, for example, an inflated configuration (FIG. 12B). That is, a material may be moved through aperture 98 and into lumen 94 such that the material enters chamber 102 through openings 100 to move balloon 88 from the uninflated configuration to the inflated configuration. In some embodiments, cylindrical portion 84 comprises a membrane 104 that seals lumen 94 to prevent the material from contacting spool 86. Cable 90 extends through membrane 104, as shown in FIG. 11. When balloon 88 is in the inflated configuration, balloon 88 has a maximum diameter that is greater than the maximum diameter of balloon 88 when balloon 88 is in the uninflated configuration. In some embodiments, openings 100 are spaced apart from one another longitudinally along a longitudinal axis L2 defined by cylindrical portion 84, as shown in FIG. 11. In some embodiments, openings 100 are spaced apart from one another radially about a circumference of cylindrical portion 84, as shown in FIG. 12.

In some embodiments, lumen 94 may be disposed at alternate orientations, relative to longitudinal axis L2, such as, for example, parallel, transverse and/or other angular orientations such as acute or obtuse, co-axial and/or may be offset or staggered. In some embodiments, lumen 94 may have various cross section configurations, such as, for example, circular, oval, oblong, triangular, rectangular, square, polygonal, irregular, uniform, non-uniform, variable, tubular and/or tapered. In some embodiments, openings 100 can have various shape configurations, such as, for example, circular, oval, oblong, polygonal, irregular, uniform, non-uniform, variable and/or tapered. In some embodiments, openings 100 may be disposed at alternate orientations, relative to longitudinal axis L2, such as, for example, transverse, perpendicular and/or other angular orientations such as acute or obtuse, co-axial and/or may be offset or staggered. In some embodiments, end wall 92 closes off lumen 94 such that the material that is used to move balloon 88 from the uninflated configuration to the inflated configuration remains within lumen 94 and/or chamber 102, and does not escape through end wall 92. In some embodiments, balloon 88 may the same or similar to balloon 34, balloon 52 and/or balloon 70 and may be made of the same or similar materials and/or have the same or similar characteristics as those discussed above with regard to balloon 34, balloon 52 and/or balloon 70.

Figure 12A:
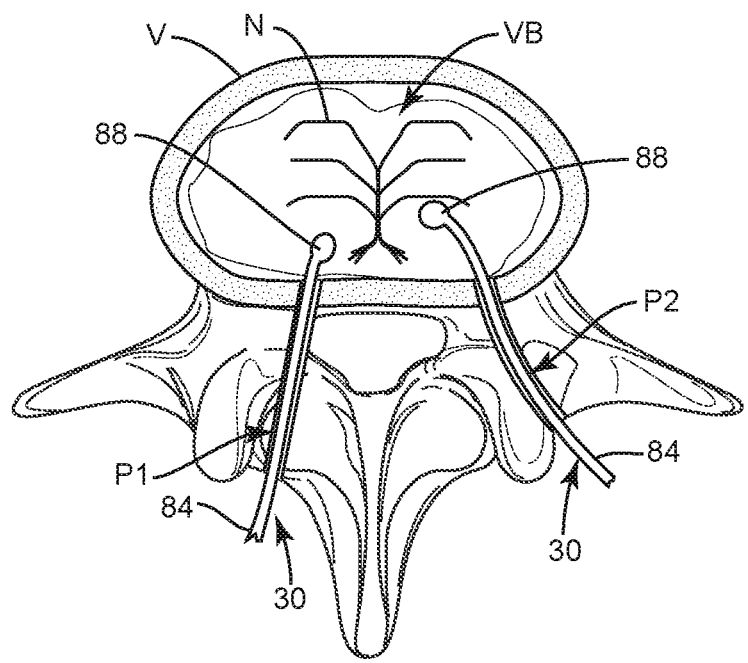
FIG. 12A is a top, cross sectional view of the vertebra shown in FIG. 3 with components of one of the balloon catheters discussed herein inserted into the vertebra.
Figure 12B:
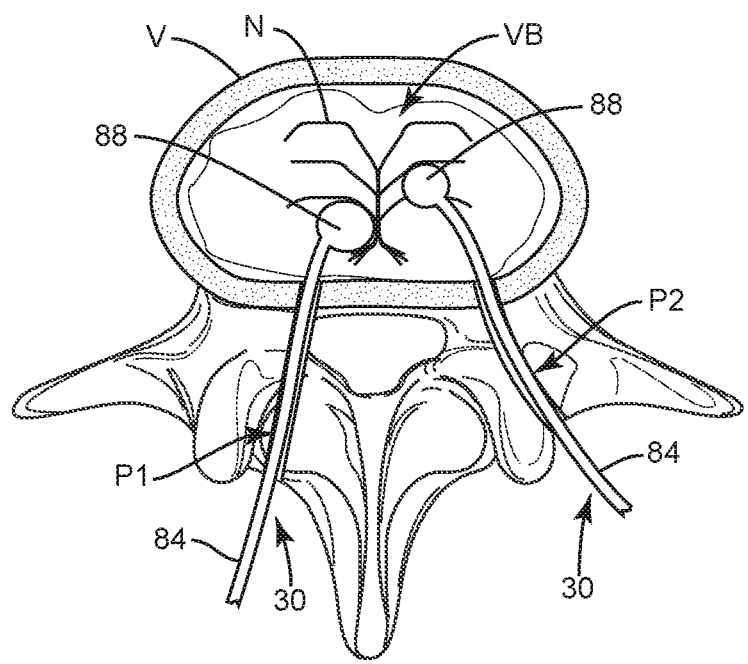
FIG. 12B is a top, cross sectional view of the vertebra shown in FIG. 3 with components of one of the balloon catheters discussed herein inserted into the vertebra.

Referring to FIGS. 12A and 12B, in use, balloon catheter 30 may be moved along pathway P1 and/or pathway P2 such that balloon 88 moves through opening O1 and/or opening O2 and into vertebral body VB, as shown in FIG. 12A. In some embodiments, balloon catheter 30 is moved between the first and second configurations discussed above one or a plurality of times in order to bend cylindrical portion 84 to conform cylindrical portion to curves along pathway P2, for example. That is, spool 86 is rotated relative to cylindrical portion 84 about rotation axis RA in direction A and/or direction B to cause cable 90 to wind and unwind from spool 86, thus causing the distal end of cylindrical portion 84 to straighten and bend, as required. In some embodiments, steering balloon catheter 30 comprises deflecting at least a portion of balloon catheter 30 in a single plane, such as, for example, plane P shown in FIG. 12.

In some embodiments, balloon 88 is moved into vertebral body VB when balloon 88 is in the uninflated configuration, as shown in FIG. 12A. In some embodiments, pathways P1 and P2 and openings O1 and O2 each have a maximum width that is greater than that of balloon 88 when balloon 88 is in the uninflated configuration to allow balloon 88 to move easily through pathways P1 and P2 and openings O1 and O2 and into vertebral body VB to reach the target location/treatment zone. In some embodiments, the outer surface of balloon 88 is spaced apart from nerve N when balloon 88 is in the uninflated configuration, as shown in FIG. 12A. In some embodiments, at least a portion of the outer surface of balloon 88 may contact at least a portion of nerve N when balloon 88 is in the uninflated configuration.

Once positioned within vertebral body VB, balloon 88 is moved from the uninflated configuration (FIG. 12A) to the inflated configuration (FIG. 12B). In particular, material may be moved through aperture 98 and into lumen 94. The material moves from lumen 94 and into chamber 102 through openings 100 to move balloon 88 from the uninflated configuration to the inflated configuration, as discussed above. This allows balloon 88 to get as close as possible to the treatment zone. In some embodiments, the material moved through aperture 98 and lumen 94 and into chamber 102 through openings 100 to move balloon 88 from the uninflated configuration to the inflated configuration is a chemical denervation agent, such as, for example, one or more of the chemical denervation agents discussed herein, and balloon 88 comprises a porous material. That is, balloon 88 is a porous balloon that is at least partially filled with the chemical denervation agent such that when balloon 88 is positioned at, in or near the treatment zone, the chemical denervation agent is released from balloon 88 so as to ablate and/or denervate nerve N, thus reducing back and/or neck pain in the patient. In some embodiments, this configuration prolongs the release of the chemical denervation agent. That is, the chemical denervation agent is released from balloon 88 over time, rather than all at once. In some embodiments, porous balloon 88 delivers the chemical denervation agent so that the chemical denervation agent directly contacts nerve N. In some embodiments, the porous balloon 88 is configured such that the chemical denervation agent will not move through pores of the porous balloon 88 until the pressure within chamber 102 reaches a pre-determined threshold. For example, the chemical denervation agent may be moved through aperture 98 and lumen 94 and into chamber 102 through openings 100 using a first pressure to move balloon 88 from the uninflated configuration to the inflated configuration. As such, when balloon 88 is in the inflated configuration, the pressure within chamber 102 will be the same or approximately the same as the first pressure. When the pressure within chamber 102 is the same or approximately the same as the first pressure, the chemical denervation agent is prevented from moving through pores of balloon 88. Additional amounts of the chemical denervation agent and/or another material may then be moved through aperture 98 and lumen 94 and into chamber 102 through openings 100 to further inflate balloon 88, which will increase the pressure within chamber 102 to a second pressure that is greater than the first pressure. When the pressure within chamber 102 is the same or approximately the same as the second pressure, the chemical denervation agent is able to move through pores of balloon 88 and either directly contact nerve N or migrate to nerve N.

Figure 13:
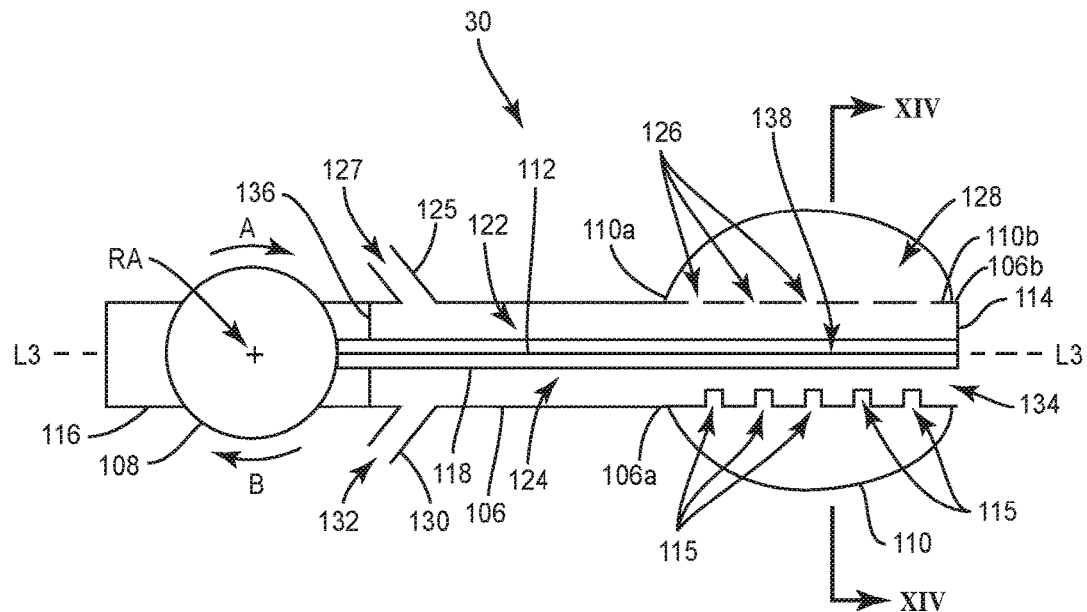
FIG. 13 is a side, cross sectional view of components of one embodiment of a balloon catheter in accordance with the principles of the present disclosure.
Figure 13A:
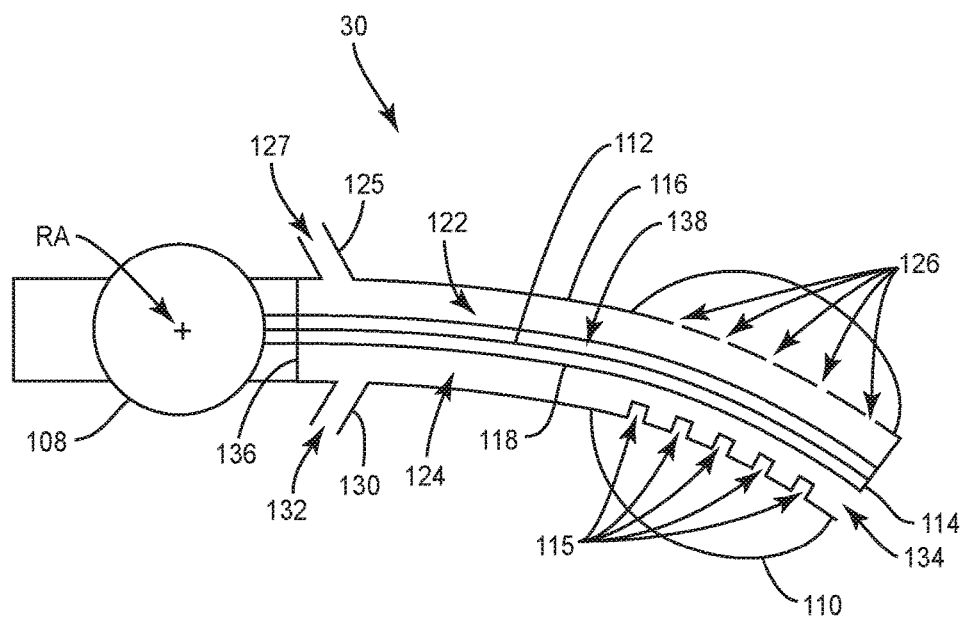
FIG. 13A is a side, cross sectional view of the balloon catheter shown in FIG. 13.
Figure 14:
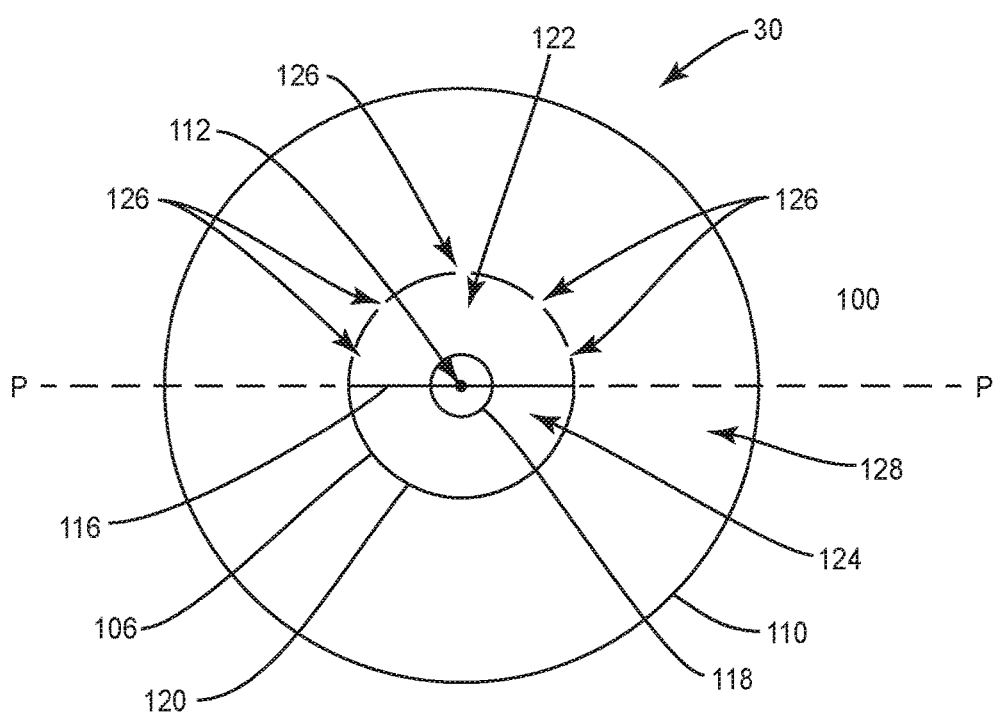
FIG. 14 is a cross sectional view of the balloon catheter shown in FIG. 13 taken along lines XIV-XIV in FIG. 13.

In one embodiment, shown in FIGS. 13, 13A and 14, balloon catheter 30 is steerable, as discussed herein, and includes a cylindrical portion 106. Cylindrical portion 106 comprises a spool 108 rotatably coupled to a proximal end of cylindrical portion 106 and a balloon 110 coupled to a distal end of cylindrical portion 106. Spool 108 is rotatable about a rotation axis RA in a first direction, such as, for example, the direction shown by arrow A in FIG. 13 and an opposite second direction, such as, for example, the direction shown by arrow B in FIG. 13. A first end of a cable 112 is wound about spool 108 and a second end of cable 112 is fixed to a distal end wall 114 of cylindrical portion 106. Rotating spool 108 relative to cylindrical portion 106 about rotation axis RA in one direction, such as, for example, direction A or B, will cause more cable 112 to wind about spool 108, thus causing the distal end of cylindrical portion 106 to bend, similar to the embodiment shown in FIG. 11A. Rotating spool 108 relative to cylindrical portion 106 about rotation axis RA in another direction, such as, for example, direction A or B, will cause more cable 112 to unwind from spool 108, thus causing the distal end of cylindrical portion 106 to straighten, similar to the embodiment shown in FIG. 11. For example, balloon catheter 30 is movable between a first configuration, shown in FIG. 13, in which cylindrical portion 106 is straight, and a second configuration, shown in FIG. 13A, in which cylindrical portion 106 is bent. As discussed above, balloon catheter 30 is movable between the first and second configurations by rotating spool 108 to wind and unwind cable 112. In some embodiments, the distal end of cylindrical portion 106 comprises one or a plurality of notches 115 configured to facilitate bending of cylindrical portion 106. That is, notches 115 will help cylindrical portion 106 bend to move balloon catheter 30 from the first configuration to the second configuration. Cylindrical portion 106 is flexible to avow cylindrical portion 106 to bend as cylindrical portion 106 moves from the first configuration to the second configuration and is navigated through a patient's anatomy. In some embodiments, cylindrical portion 106 comprises a memory material, such as, for example, nitinol, to help cylindrical portion 106 return to the first configuration from the second configuration.

Cylindrical portion 106 extends through balloon 110, as shown in FIGS. 13 and 13A. That is, a first end 110a of balloon 110 is coupled to a first section 106a of cylindrical portion 106 and an opposite second end 110b of balloon 110 is coupled to a second section 106b of cylindrical portion 106. Cylindrical portion 106 comprises an outer shaft 116 and an inner shaft 118 positioned within outer shaft 116. In some embodiments, inner shaft 118 is coaxial and/or concentric with outer shaft 116. Inner shaft 118 is spaced apart from outer shaft 118 such that a space between inner shaft 118 and outer shaft 116 defines a passageway. The passageway is divided by a wall 120, as shown in FIG. 14. Wall 120 divides the passageway into a first lumen 122 and a second lumen 124. That is, first lumen 122 is spaced apart from second lumen 124 by wall 120 such that first lumen 122 is not in communication with second lumen 124. In some embodiments, wall 120 extends the entire length of cylindrical portion 106. First lumen 122 is parallel to second lumen 124. First and second lumens 122, 124 are disposed side-by-side. That is, first lumen 122 is not coaxial and/or concentric with second lumen 124. In some embodiments, wall 120 divides cylindrical portion 106 such that first lumen 122 is the same size as second lumen 124. In some embodiments, wall 120 divides cylindrical portion 106 such that first lumen 122 is has a larger cross section than second lumen 124. In some embodiments, wall 120 divides cylindrical portion 106 such that first lumen 122 is has a smaller cross section than second lumen 124. In some embodiments, balloon 110 may the same or similar to balloon 34, balloon 52, balloon 70 and/or balloon 88 and may be made of the same or similar materials and/or have the same or similar characteristics as those discussed above with regard to baboon 34, balloon 52, balloon 70 and/or balloon 88.

Outer shaft 116 comprises a first port 125 that is in communication with first lumen 122. Port 125 includes a first aperture 127. A distal end of outer shaft 116 comprises one or a plurality of openings 126 that are in communication with an internal chamber 128 of balloon 110 such that a material that is injected through first aperture 127 and into first lumen 122 will enter chamber 128 through openings 126 to move balloon 110 from an unexpanded configuration, such as, for example, an uninflated configuration (FIG. 14A) to an expanded configuration, such as, for example, an inflated configuration (FIG. 14B). That is, a material may be moved through first aperture 127, first lumen 122 and openings 126 and into chamber 128 to move balloon 110 from the uninflated configuration to the inflated configuration. When balloon 110 is in the inflated configuration, balloon 110 has a maximum diameter that is greater than the maximum diameter of balloon 110 when balloon 110 is in the uninflated configuration. In some embodiments, outer shaft 116 comprises a plurality of openings 126 that are spaced apart from one another longitudinally along a longitudinal axis L3 defined by outer shaft 116, as shown in FIG. 13. In some embodiments, outer shaft 116 comprises a plurality of openings 126 that are spaced apart from one another radially about a circumference of outer shaft 116, as shown in FIG. 14.

Outer shaft 116 comprises a second port 130 that is in communication with second lumen 124. Port 130 includes a second aperture 132. Second lumen 124 comprises an outlet 134 that extends through end wall 114. In some embodiments, a material, such as, for example, a chemical denervation agent, such as, for example, one or more of the chemical denervation agents discussed above, may be inserted through second aperture 132 and into second lumen 124 such that the material moves through second lumen 124 and out of second aperture 132 to deliver the material to a target location, such as, for example, vertebral body VB. In some embodiments, cylindrical portion 106 comprises a membrane 136 that seals first and second lumens 122, 124 to prevent any material disposed within first and second lumens 122, 124 from contacting spool 108. Inner shaft 118 extends through membrane 136, as shown in FIGS. 13 and 13A.

In some embodiments, first lumen 122 and/or second lumen 124 may be disposed at alternate orientations, relative to longitudinal axis L3, such as, for example, parallel, transverse and/or other angular orientations such as acute or obtuse, co-axial and/or may be offset or staggered. In some embodiments, first lumen 122 and/or second lumen 124 may have various cross section configurations, such as, for example, oval, oblong, triangular, rectangular, square, polygonal, irregular, uniform, non-uniform, variable, tubular and/or tapered. In some embodiments, openings 126 can have various shape configurations, such as, for example, circular, oval, oblong, polygonal, irregular, uniform, non-uniform, variable and/or tapered. In some embodiments, openings 126 may be disposed at alternate orientations, relative to longitudinal axis L3, such as, for example, transverse, perpendicular and/or other angular orientations such as acute or obtuse, co-axial and/or may be offset or staggered. In some embodiments, balloon 110 may the same or similar to any of the balloons discussed herein and may be made of the same or similar materials and/or have the same or similar characteristics as the other balloons discussed herein. In some embodiments, inner shaft 118 is hollow and defines a third lumen 138 that is spaced apart from first and second lumens 122, 124 by inner shaft 118. Third lumen 138 is not in communication with first lumen 122 or second lumen 124. End wall 114 engages inner shaft 118 at a distal end of inner shaft 118 to close off third lumen 138 at end wall 114. Cable 112 is positioned within third lumen 138.

Figure 14A:
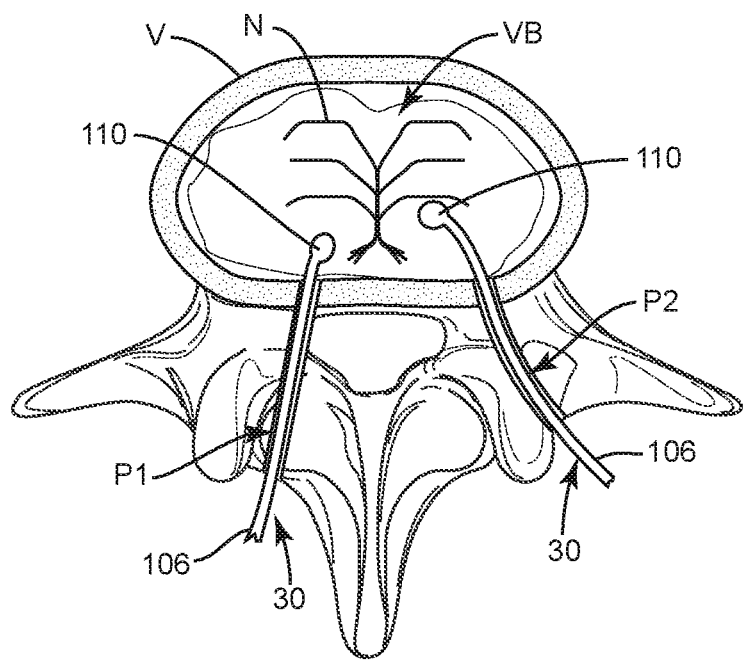
FIG. 14A is a top, cross sectional view of the vertebra shown in FIG. 3 with components of one of the balloon catheters discussed herein inserted into the vertebra.
Figure 14B:
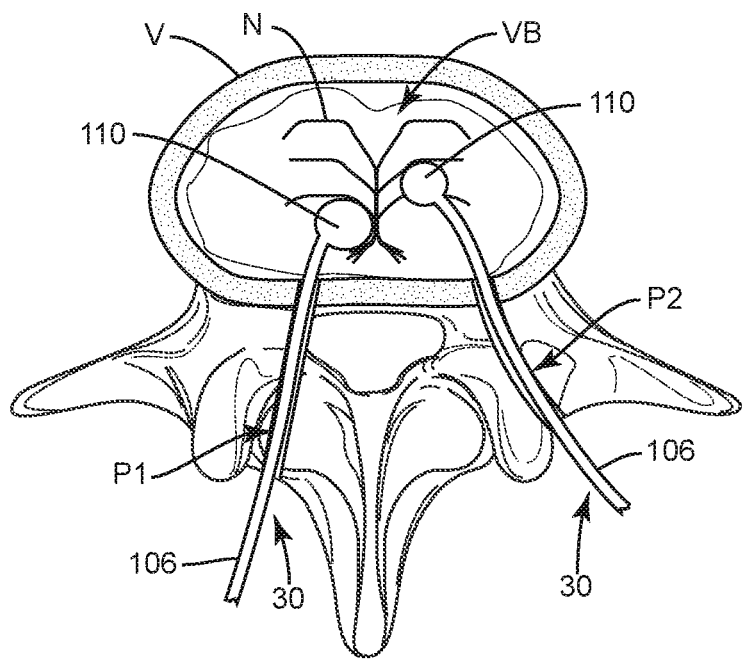
FIG. 14B is a top, cross sectional view of the vertebra shown in FIG. 3 with components of one of the balloon catheters discussed herein inserted into the vertebra.

Referring to FIGS. 14A and 14B, in use, balloon catheter 30 may be moved along pathway P1 and/or pathway P2 such that balloon 110 moves through opening O1 and/or opening O2 and into vertebral body VB, as shown in FIG. 14A. In some embodiments, balloon catheter 30 is moved between the first and second configurations discussed above one or a plurality of times in order to bend cylindrical portion 84 to conform cylindrical portion to curves along pathway P2, for example. That is, spool 108 is rotated relative to cylindrical portion 106 about rotation axis RA in direction A and/or direction B to cause cable 112 to wind and unwind from spool 108, thus causing the distal end of cylindrical portion 106 to straighten and bend, as required. In some embodiments, steering balloon catheter 30 comprises deflecting at least a portion of balloon catheter 30 in a single plane, such as, for example, plane P shown in FIG. 14.

In some embodiments, balloon 110 is moved into vertebral body VB when balloon 110 is in the uninflated configuration, as shown in FIG. 14A. In some embodiments, pathways P1 and P2 and openings O1 and O2 each have a maximum width that is greater than that of balloon 110 when balloon 110 is in the uninflated configuration to allow balloon 88 to move easily through pathways P1 and P2 and openings O1 and O2 and into vertebral body VB to reach the target location/treatment zone. In some embodiments, the outer surface of balloon 110 is spaced apart from nerve N when balloon 110 is in the uninflated configuration, as shown in FIG. 14A. In some embodiments, at least a portion of the outer surface of balloon 110 may contact at least a portion of nerve N when balloon 110 is in the uninflated configuration.

Once positioned within vertebral body VB, balloon 110 is moved from the uninflated configuration (FIG. 14A) to the inflated configuration (FIG. 14B). In particular, material may be moved through aperture 127 and into first lumen 122. The material moves from first lumen 122 and into chamber 128 through openings 126 to move balloon 110 from the uninflated configuration to the inflated configuration, as discussed above. This allows balloon 110 to get as close as possible to the treatment zone. In some embodiments, the material moved through aperture 127 and first lumen 122 and into chamber 128 through openings 126 to move balloon 110 from the uninflated configuration to the inflated configuration is a chemical denervation agent, such as, for example, one or more of the chemical denervation agents discussed herein. In some embodiments, balloon 110 comprises a porous material such that the chemical denervation agent will exit balloon 110 to treat nerve N in the manner discussed with regard to the porous balloons discussed herein. In some embodiments, the material moved through aperture 127 and first lumen 122 and into chamber 128 through openings 126 to move balloon 110 from the uninflated configuration to the inflated configuration is a conventional inflation material, such as, for example, one or more of the conventional inflation materials discussed above.

In some embodiments, a chemical denervation agent, such as, for example, one or more of the chemical denervation agents discussed herein is moved through aperture 132 and into second lumen 124 such that the chemical denervation agent exits second lumen 124 through outlet 134 to deliver the chemical denervation agent at, in or near nerve N to ablate and/or denervate nerve N as discussed herein.

Figure 15:
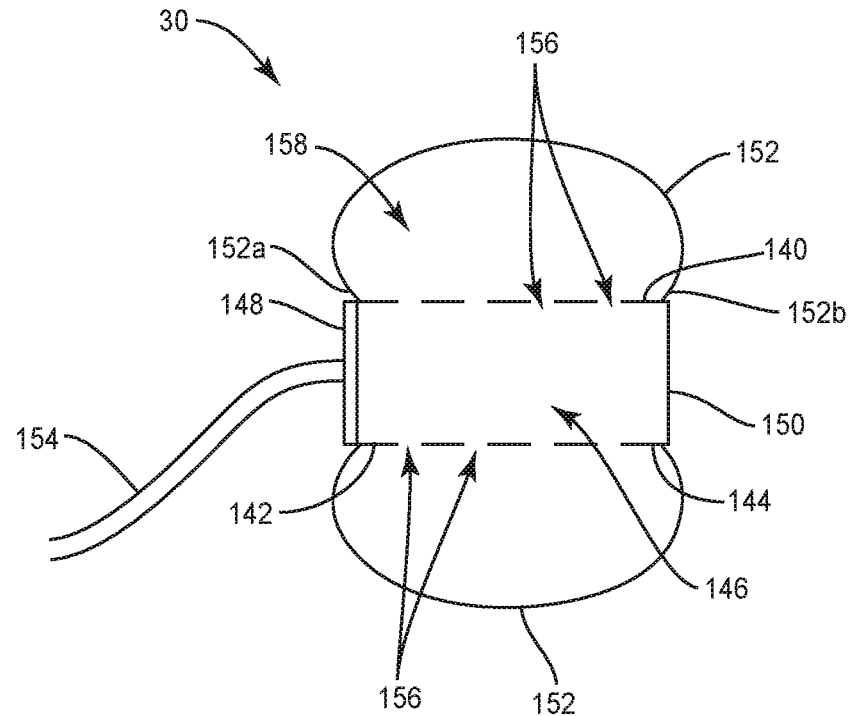
FIG. 15 is a side, cross sectional view of components of one embodiment of a balloon catheter in accordance with the principles of the present disclosure.
Figure 15A:
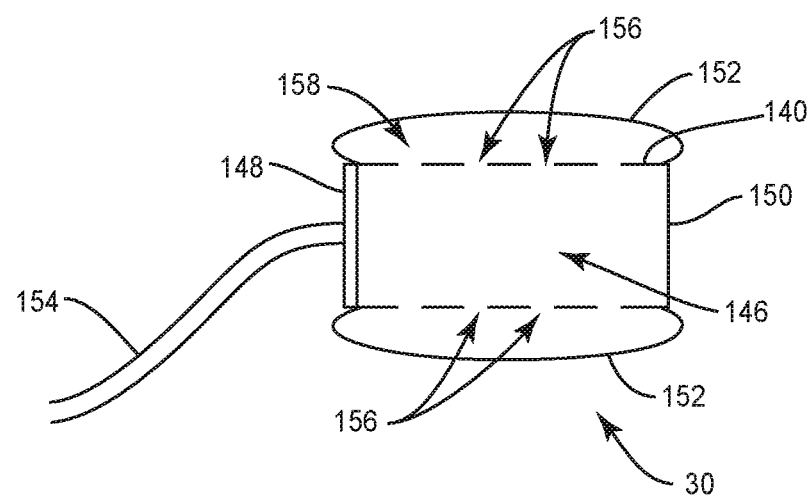
FIG. 15A is a side, cross sectional view of the balloon catheter shown in FIG. 15.

In one embodiment, shown in FIGS. 15 and 15A, balloon catheter 30 is implantable within the patient's anatomy. That is, at least a portion of balloon catheter 30 is configured to remain within the patient after an incision in the patient through which balloon catheter 30 is inserted is closed. Balloon catheter 30 comprises a shaft 140 extending between a first end 142 and an opposite second end 144. Shaft 140 is hollow such that an inner surface of shaft 140 defines a cavity 146. First end 142 comprises a one-way valve 148 that allows a material, such as, for example, a chemical denervation agent or conventional inflation material to move into cavity 146 through valve 148, but does not avow the material to exit cavity 146 through valve 148. Second end 144 comprises an end wall 150 that faces valve 148. End wall 150 acts to close cavity 146 at second end 144. In some embodiments, shaft 140 comprises a biodegradable and/or bioresorbable material such that shaft 140 can remain within a patient after a surgical procedure is completed without the need to remove shaft 140 at a later time.

A balloon 152 is coupled to an outer surface of shaft 140. A first end 152a of balloon 152 is coupled to first end 142 and an opposite second end 152b of balloon 152 is coupled to second end 144 such that shaft 140 extends through balloon 152. Balloon catheter 30 comprises a delivery tube 154 that is removably coupled to valve 148. Delivery tube 154 is configured to deliver a material, such as, for example, one or more of the chemical denervation agents discussed herein through valve 148 and into cavity 146. Shaft 140 comprises one or a plurality of openings 156 that are in communication with an internal chamber 158 of balloon 152 such that the material in delivery tube 154 can move through valve 148 and cavity 146 and will enter chamber 158 through openings 156 to move balloon 152 from an unexpanded configuration, such as, for example, an uninflated configuration (FIG. 15A) to an expanded configuration, such as, for example, an inflated configuration (FIG. 15). When balloon 152 is in the inflated configuration, balloon 152 has a maximum diameter that is greater than the maximum diameter of balloon 152 when balloon 152 is in the uninflated configuration. In some embodiments, balloon 152 comprises a biodegradable and/or bioresorbable material such that balloon 152 can remain within a patient after a surgical procedure is completed without the need to remove balloon 152 at a later time. In some embodiments, balloon 152 may the same or similar to balloon 34, balloon 52, balloon 70, balloon 88 and/or balloon 110 and may be made of the same or similar materials and/or have the same or similar characteristics as those discussed above with regard to balloon 34, balloon 52, balloon 70, balloon 88 and/or balloon 110.

Figure 16:
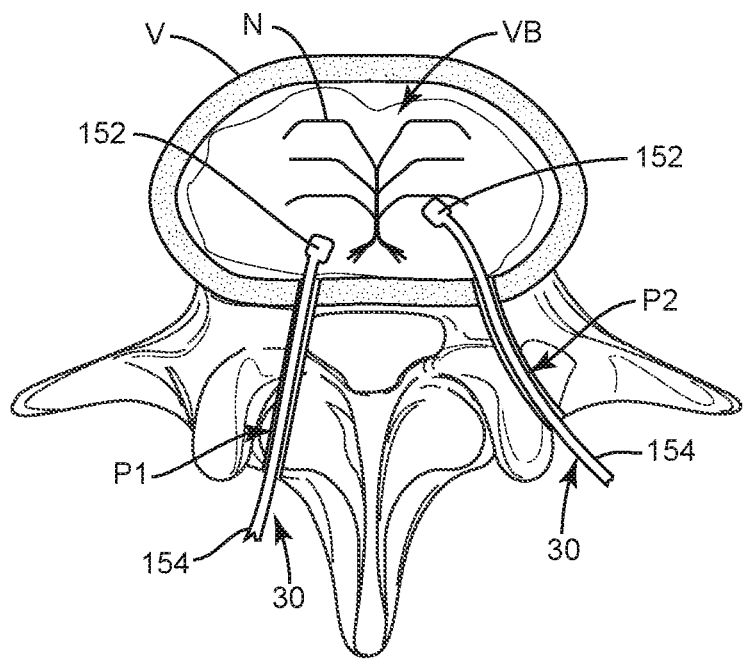
FIG. 16 is a top, cross sectional view of the vertebra shown in FIG. 3 with components of the balloon catheter shown in FIG. 15 inserted into the vertebra.

In use, balloon catheter 30 may be moved along pathway P1 and/or pathway P2 such that balloon 152 moves through opening O1 and/or opening O2 and into vertebral body VB, as shown in FIG. 16. In some embodiments, pathways P1 and P2 and openings O1 and O2 each have a maximum width that is greater than that of balloon 52 when balloon 152 is in the uninflated configuration to avow balloon 152 to move easily through pathways P1 and P2 and openings O1 and O2 and into vertebral body VB to reach the target location/treatment zone. In some embodiments, the outer surface of balloon 152 is spaced apart from nerve N when balloon 152 is in the uninflated configuration, as shown in FIG. 16. In some embodiments, at least a portion of the outer surface of balloon 152 may contact at least a portion of nerve N when balloon 152 is in the uninflated configuration.

Figure 17:
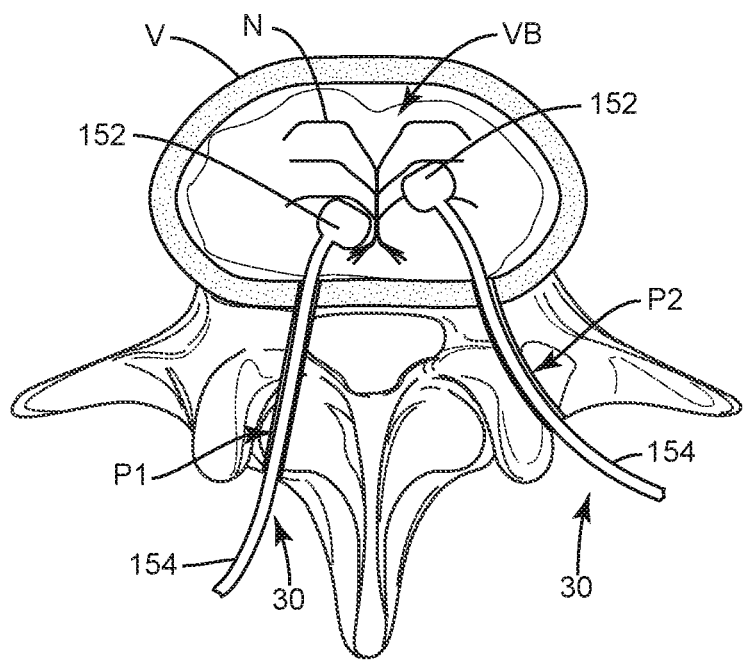
FIG. 17 is a top, cross sectional view of the vertebra shown in FIG. 3 with components of the balloon catheter shown in FIG. 15 inserted into the vertebra.
Figure 18:
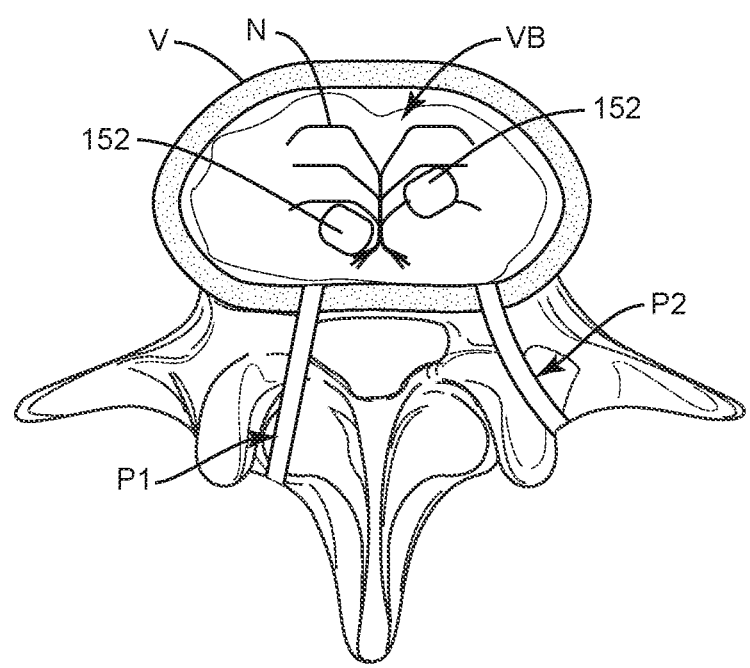
FIG. 18 is a top, cross sectional view of the vertebra shown in FIG. 3 with components of the balloon catheter shown in FIG. 15 inserted into the vertebra.

Once positioned within vertebral body VB, balloon 152 is moved from the uninflated configuration (FIG. 16) to the inflated configuration (FIG. 17). In particular, material may be moved through delivery tube 154, valve 148 and cavity 146 and into chamber 158 through openings 156 to move balloon 152 from the uninflated configuration to the inflated configuration, as discussed above. This allows balloon 152 to get as close as possible to the treatment zone. In some embodiments, the material that is moved through delivery tube 154, valve 148 and cavity 146 and into chamber 158 through openings 156 is a chemical denervation agent, such as, for example, one or more of the chemical denervation agents discussed herein. In some embodiments, delivery tube 154 is detached from shaft 140 and/or valve 148 and is removed from the patient, as shown in FIG. 18. In that valve 148 prevents the chemical denervation agent from exiting cavity 146 or chamber 158 through valve 148, balloon 152 remains in the inflated configuration. The incision that was made to insert balloon catheter 30 may then be closed, with balloon 152 remaining within the patient after the incision is closed.

In some embodiments, balloon 152 comprises a porous material. That is, balloon 152 is a porous balloon that is at least partially filled with the chemical denervation agent such that when balloon 152 is positioned at, in or near the treatment zone, the chemical denervation agent is released from balloon 152 so as to ablate and/or denervate nerve N, thus reducing back and/or neck pain in the patient. In some embodiments, this configuration prolongs the release of the chemical denervation agent. That is, the chemical denervation agent is released from balloon 152 over time, rather than all at once. In some embodiments, porous balloon 152 delivers the chemical denervation agent so that the chemical denervation agent directly contacts nerve N. In some embodiments, porous balloon 152 delivers the chemical denervation agent so that the chemical denervation agent within about 0.05 mm to about 5 mm of nerve N. In some embodiments, porous balloon 152 delivers the chemical denervation agent so that the chemical denervation agent within about 1 mm of nerve N.

Figure 19:
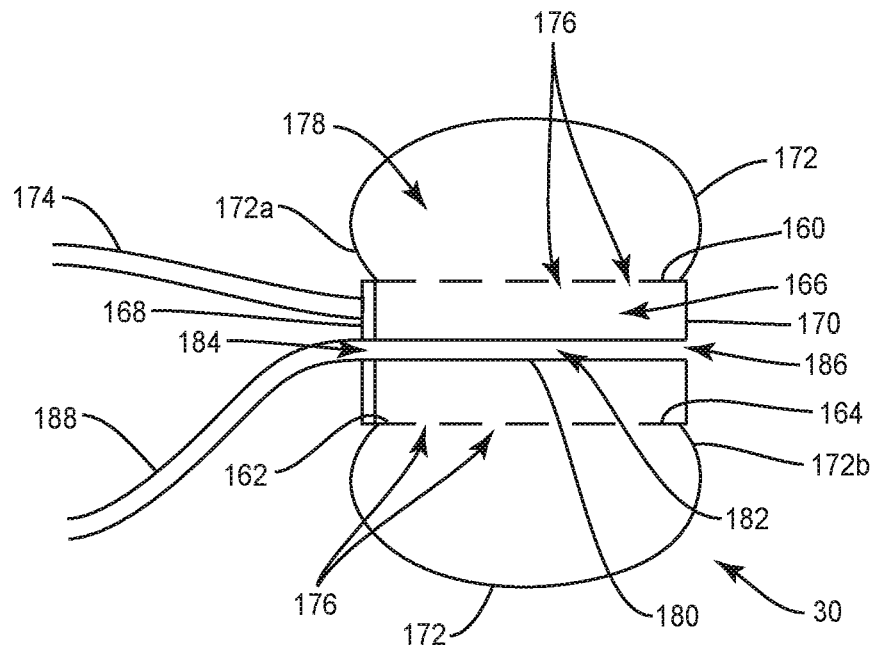
FIG. 19 is a side, cross sectional view of components of one embodiment of a balloon catheter in accordance with the principles of the present disclosure.
Figure 19A:
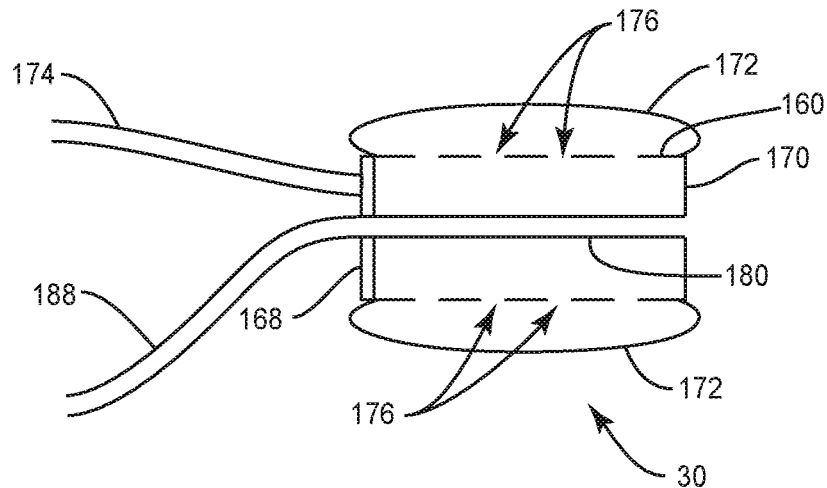
FIG. 19A is a side, cross sectional view of the balloon catheter shown in FIG. 15.

In one embodiment, shown in FIGS. 19 and 19A, balloon catheter 30 comprises an outer shaft 160 extending between a first end 162 and an opposite second end 164. Outer shaft 160 is hollow such that an inner surface of outer shaft 160 defines a cavity 166. First end 162 comprises a one-way valve 168 that allows a material, such as, for example, a chemical denervation agent or conventional inflation material to move into cavity 166 through valve 168, but does not allow the material to exit cavity 166 through valve 168. Second end 164 comprises an end wall 170 that faces valve 168. End wall 170 acts to close cavity 166 at second end 164. In some embodiments, outer shaft 160 comprises a biodegradable and/or bioresorbable material such that outer shaft 160 can remain within a patient after a surgical procedure is completed without the need to remove outer shaft 160 at a later time.

A balloon 172 is coupled to an outer surface of outer shaft 160. A first end 172a of balloon 172 is coupled to first end 162 and an opposite second end 172b of balloon 172 is coupled to second end 164 such that outer shaft 160 extends through balloon 172. Balloon catheter 30 comprises a delivery tube 174 that is removably coupled to valve 168. Delivery tube 174 is configured to deliver a material, such as, for example, one or more of the chemical denervation agents and/or one or more of the conventional inflation materials discussed herein can move from delivery tube 174, through valve 168 and into cavity 166. Outer shaft 160 comprises one or a plurality of openings 176 that are in communication with an internal chamber 178 of balloon 172 such that the material in delivery tube 174 can move through valve 168 and cavity 166 and will enter chamber 178 through openings 176 to move balloon 172 from an unexpanded configuration, such as, for example, an uninflated configuration (FIG. 19A) to an expanded configuration, such as, for example, an inflated configuration (FIG. 19). When balloon 172 is in the inflated configuration, balloon 172 has a maximum diameter that is greater than the maximum diameter of balloon 172 when balloon 172 is in the uninflated configuration. In some embodiments, balloon 172 comprises a biodegradable and/or bioresorbable material such that balloon 172 can remain within a patient after a surgical procedure is completed.

Balloon catheter 30 comprises an inner shaft 180 positioned within outer shaft 160. Inner shaft 180 is hollow and extends through valve 168 and end wall 170. An inner surface of inner shaft 180 defines a lumen 182. Lumen 182 is spaced apart from cavity 166 by inner shaft 180. Lumen 182 includes an inlet 184 at a first end of inner shaft 180 and an outlet 186 at an opposite second end of inner shaft 180. A second delivery tube 188 may be coupled to inlet 184 to move a material, such as, for example, one or more of the chemical denervation agents discussed herein from second delivery tube 188, through inlet 184, into lumen 182 and out of outlet 186. In some embodiments, second delivery tube 188 may be removably coupled to inlet 184.

Figure 20:
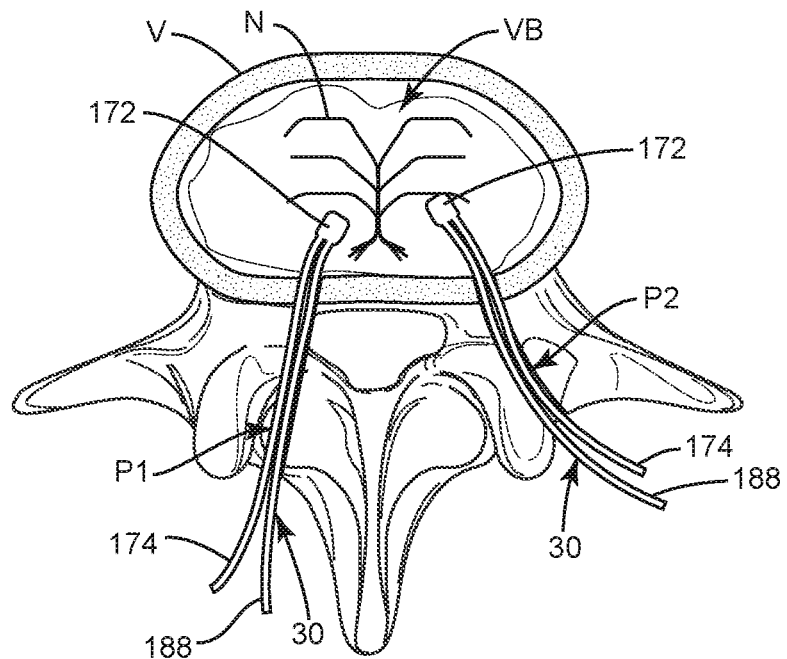
FIG. 20 is a top, cross sectional view of the vertebra shown in FIG. 3 with components of the balloon catheter shown in FIG. 19 inserted into the vertebra.

In use, balloon catheter 30 may be moved along pathway P1 and/or pathway P2 such that balloon 172 moves through opening O1 and/or opening O2 and into vertebral body VB, as shown in FIG. 20. In some embodiments, pathways P1 and P2 and openings O1 and O2 each have a maximum width that is greater than that of balloon 172 when balloon 172 is in the uninflated configuration to avow balloon 172 to move easily through pathways P1 and P2 and openings O1 and O2 and into vertebral body VB to reach the target location/treatment zone. In some embodiments, the outer surface of balloon 172 is spaced apart from nerve N when balloon 172 is in the uninflated configuration, as shown in FIG. 19A. In some embodiments, at least a portion of the outer surface of balloon 172 may contact at least a portion of nerve N when balloon 172 is in the uninflated configuration.

Figure 21:
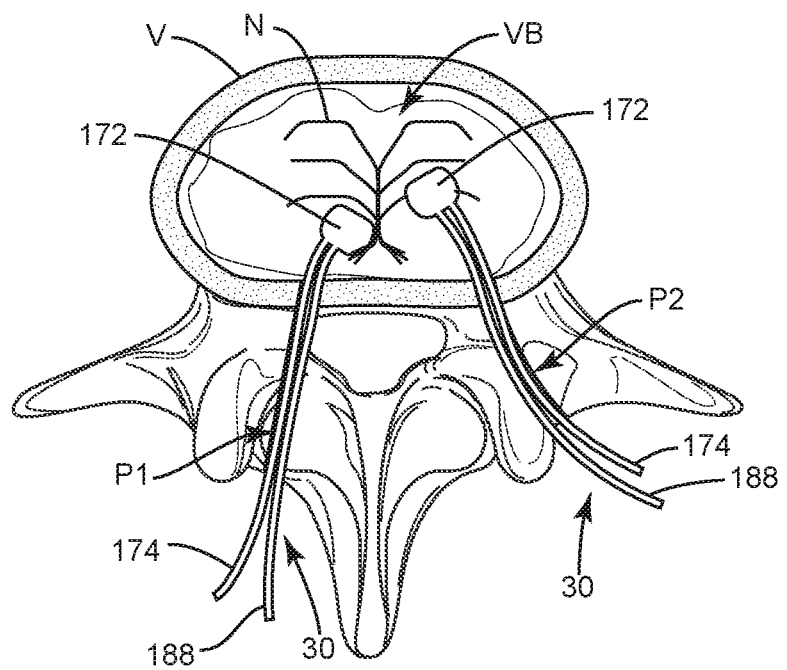
FIG. 21 is a top, cross sectional view of the vertebra shown in FIG. 3 with components of the balloon catheter shown in FIG. 19 inserted into the vertebra.

Once positioned within vertebral body VB, balloon 172 is moved from the uninflated configuration (FIG. 20) to the inflated configuration (FIG. 21). In particular, material may be moved through delivery tube 174, valve 168 and cavity 166 and into chamber 178 through openings 176 to move balloon 172 from the uninflated configuration to the inflated configuration, as discussed above. This allows balloon 172 to get as close as possible to the treatment zone. In some embodiments, the material that is moved through delivery tube 174, valve 168 and cavity 166 and into chamber 178 through openings 176 is a conventional inflation material, such as, for example, one or more of the conventional inflation materials discussed herein. In some embodiments, the material that is moved through delivery tube 174, valve 168 and cavity 166 and into chamber 178 through openings 176 is a chemical denervation agent, such as, for example, one or more of the chemical denervation agents discussed herein. In embodiments wherein a chemical denervation agent, balloon 172 may comprise a porous material such that the chemical denervation agent can be released through pores in balloon 172 over time, as with the other porous balloons discussed herein. A chemical denervation agent, such as, for example, one or more of the chemical denervation agents discussed herein may be moved through second delivery tube 188, inlet 184 and lumen 182 such that the chemical denervation agent exits outlet 186 at, in or near nerve N to ablate and/or denervate nerve N, as discussed herein.

Figure 22:
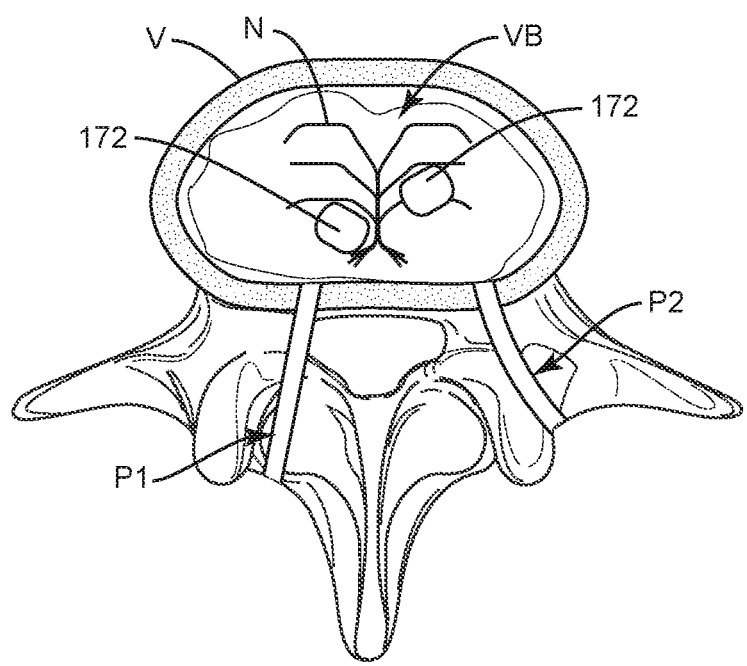
FIG. 22 is a top, cross sectional view of the vertebra shown in FIG. 3 with components of the balloon catheter shown in FIG. 19 inserted into the vertebra.

In some embodiments, delivery tube 174 and/or second delivery tube 188 may be detached from inlet 184 and/or valve 148 and removed from the patient, as shown in FIG. 22. In that valve 168 prevents the conventional inflation material and/or chemical denervation agent from exiting cavity 166 or chamber 178 through valve 168, balloon 172 remains in the inflated configuration. The incision that was made to insert balloon catheter 30 may then be closed, with balloon 172 remaining within the patient after the incision is closed.

In any of the embodiments discussed herein, balloon catheter 30 may be inserted into the patient through an access device, such as, for example a cannula. In some embodiments, the cannula comprises a lumen configured for disposal of balloon catheter 30. In some embodiments, the cannula can be positioned through pathway P1 and/or pathway P2 such that a distal end of the cannula extends through opening O1 and/or opening O2 and into vertebral body VB.

In some embodiments, a kit containing one or more components of balloon catheter 30 is provided. The kit may include components from any of the embodiments discussed herein. The kit may also include one or more of the chemical denervation agents discussed herein and/or one or more of the conventional inflation materials discussed herein. In some embodiments, the kit includes an access device, such as, for example, the cannula discussed above. In some embodiments, the kit comprises a plurality of cannulas, each having a different length. In some embodiments, the kit includes instructions for chemically ablating and/or denervating at least a portion of a nerve, such as, for example, a basivertebral nerve using the contents of the kit.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for treating back pain in a patient in need of such treatment, the method comprising:
providing a balloon catheter having a proximal first end, an opposite distal second end, a mid-longitudinal axis extending through the proximal first end and the distal second end, an outer shaft portion, an inner shaft portion, and a porous balloon portion, the outer shaft portion and the inner shaft portion being coaxial with the mid-longitudinal axis and extending between the proximal first end and the distal second end, the inner shaft portion being positioned within the outer shaft portion, a first lumen being formed between the outer shaft portion and the inner shaft portion, a second lumen being formed through the inner shaft portion, the balloon portion being attached to the outer shaft portion at a first location at the distal second end and a second location between the proximal first end and the distal second end, the outer shaft portion including apertures formed therethrough adjacent the distal second end, and the balloon portion including porosities formed therein, the apertures in the outer shaft portion affording communication between the first lumen and an interior of the balloon portion, and the porosities formed in the balloon portion affording communication between the interior of the balloon and an exterior of the balloon portion;

positioning the distal second end of the balloon catheter in or adjacent to a treatment zone containing a basivertebral nerve;

transferring a first chemical denervation agent at a first pressure through the first lumen, through the apertures in the outer shaft portion, and into the interior of the balloon portion to inflate the balloon portion;

after the inflation of the balloon portion, increasing the first chemical denervation agent to a second pressure greater than the first pressure to transfer the first chemical denervation agent from the interior to the exterior of the balloon portion and the treatment zone via the porosities formed in the balloon portion;

transferring a second denervation agent through the second lumen to the treatment zone; and chemically ablating at least a portion of the basivertebral nerve with the first and second denervation agents.

2. The method of claim 1, wherein the treatment zone is a vertebra, and further comprising positioning the balloon portion of the balloon catheter within the vertebra.

3. The method of claim 1, wherein the treatment zone is a vertebra, and the inflation of the balloon portion moves the balloon portion from an unexpanded configuration to an expanded configuration within the vertebra.

4. The method of claim 1, wherein the second lumen includes a port adjacent the distal second end, and transferring the second chemical denervation agent comprises moving the second chemical denervation agent out of the port.

5. The method of claim 1, further comprising creating a curved path for the balloon catheter to the treatment zone, and positioning the distal second end of the balloon catheter comprises moving the balloon portion along the curved path until the balloon portion is positioned within the vertebra.

6. The method of claim 1, wherein the balloon portion is at least partially coated with a third chemical denervation agent.

7. The method of claim 1, wherein the exterior of the balloon portion is at least partially coated with a third chemical denervation agent, and further comprising contacting a portion of the treatment zone with the exterior of the balloon portion.

8. The method of claim 1, wherein at least one of the first chemical denervation agent and the second chemical denervation agent is delivered within 1 mm of the basivertebral nerve.

9. The method of claim 1, wherein the balloon catheter is at least partially steerable, and further comprising creating a curved path from an incision to the treatment zone and actively steering the balloon catheter along the path and positioning the balloon portion in or adjacent to the vertebra.

10. The method of claim 9, wherein the steerable catheter is deflectable in only one plane.

11. The method of claim 1, wherein the second chemical denervation agent comprises an implantable biodegradable drug depot that releases the second chemical denervation agent in the treatment zone when implanted in the treatment zone so as to chemically ablate the basivertebral nerve over time as the chemical denervation agent is released.

12. A method for treating back pain in a patient in need of such treatment, the method comprising:

providing a balloon catheter having a proximal first end, an opposite distal second end, a mid-longitudinal axis extending through the proximal first end and the distal second end, an outer shaft portion, an inner shaft portion, and a porous balloon portion, the outer shaft portion and the inner shaft portion being coaxial with the mid-longitudinal axis and extending between the proximal first end and the distal second end, the inner shaft portion being positioned within the outer shaft portion, the balloon portion being attached to the outer shaft portion at a first location at the distal second end and a second location between the proximal first end and the distal second end;

positioning the distal second end of the balloon catheter in or adjacent to a treatment zone in a vertebra, the treatment zone containing a basivertebral nerve;

transferring a first chemical denervation agent at a first pressure through a first lumen formed between the outer shaft portion and the inner shaft portion, through apertures formed in the outer shaft portion adjacent the distal second end, and into an interior of the balloon portion to inflate the balloon portion;

after the inflation of the balloon portion, increasing the first chemical denervation to a second pressure greater than the first pressure to transfer the first chemical denervation agent from the interior to an exterior of the balloon portion and the treatment zone via porosities formed in the balloon portion;

transferring a second denervation agent through the second lumen formed through the inner shaft portion to the treatment zone; and chemically ablating at least a portion of the basivertebral nerve with the first and second denervation agents.

13. The method of claim 12, wherein the inflation of the balloon portion moves the balloon portion from an unexpanded configuration to an expanded configuration within the vertebra.

14. The method of claim 12, wherein the balloon catheter is at least partially steerable, and further comprising creating a curved path from an incision to the treatment zone and actively steering the balloon catheter along the path.

15. The method of claim 12, wherein the balloon portion is at least partially coated with a third chemical denervation agent.

16. The method of claim 12, wherein the exterior of the balloon portion is at least partially coated with a third chemical denervation agent, and further comprising contacting a portion of the treatment zone with the exterior of the balloon portion.

17. The method of claim 12, wherein at least one of the first chemical denervation agent and the second chemical denervation agent is delivered within 1 mm of the basivertebral nerve.

18. The method of claim 12, wherein the balloon catheter is at least partially steerable, and further comprising creating a curved path from an incision to the treatment zone and actively steering the balloon catheter along the path and positioning the balloon portion into the vertebra.

19. A method for treating back pain in a patient in need of such treatment, the method comprising:

inserting portions of a balloon catheter into the patient, the balloon catheter having a proximal first end, an opposite distal second end, a mid-longitudinal axis extending through the proximal first end and the distal second end, an outer shaft portion, an inner shaft portion, and a porous balloon portion, the outer shaft portion and the inner shaft portion being coaxial with the mid-longitudinal axis and extending between the proximal first end and the distal second end, the inner shaft portion being positioned within the outer shaft portion, the balloon portion being attached to the outer shaft portion at a first location at the distal second end and a second location between the proximal first end and the distal second end;

positioning the balloon portion into a vertebra in or adjacent to a treatment zone containing a basivertebral nerve;

transferring a first chemical denervation agent at first pressure through a first lumen formed between the outer shaft portion and the inner shaft portion, through apertures formed in the outer shaft portion adjacent the distal second end, and into an interior of the balloon portion to inflate the balloon portion;

after the inflation of the balloon portion, increasing the first chemical denervation to a second pressure greater than the first pressure to transfer the first chemical denervation agent from the interior to an exterior of the balloon portion and the treatment zone via porosities formed in the balloon portion;

transferring a second denervation agent through second lumen formed through the inner shaft portion to the treatment zone; and chemically ablating at least a portion of the basivertebral nerve with the first and second denervation agents.

20. The method of claim 19, wherein the balloon catheter is at least partially steerable, and further comprising creating a curved path from an incision to the treatment zone and actively steering the balloon catheter along the path.

* * * * *